United States Patent [19]
Zinner et al.

[11] Patent Number: 5,112,295
[45] Date of Patent: May 12, 1992

[54] PENILE PROSTHESIS AND METHOD

[76] Inventors: Norman R. Zinner, 23451 Madison St., Suite 340, Torrance, Calif. 90505; Arthur M. Sterling, 11748 Manorwood Dr., Baton Rouge, La. 70815

[21] Appl. No.: 769,121

[22] Filed: Sep. 30, 1991

Related U.S. Application Data

[63] Continuation of Ser. No. 511,563, Apr. 20, 1990, Pat. No. 5,069,201.

[51] Int. Cl.⁵ .............................................. A61F 5/00
[52] U.S. Cl. .................................................... 600/40
[58] Field of Search ............................................ 128/79

[56] References Cited

U.S. PATENT DOCUMENTS

| | | | |
|---|---|---|---|
| 4,267,829 | 5/1981 | Burton | 128/79 |
| 4,407,278 | 10/1983 | Burton et al. | 128/79 |
| 4,572,168 | 2/1986 | Fischell | 128/79 |
| 4,782,826 | 11/1988 | Fogarty | 128/79 |

Primary Examiner—Cary E. O'Connor
Attorney, Agent, or Firm—Rodman & Rodman

[57] ABSTRACT

The penile prosthesis includes proximal and distal end portions with an intermediate normally flexible, nondistensible, collapsible main body portion that adjoins the proximal and distal portions. The main body portion includes filler elements that, in some embodiments of the invention, limit radial expansion of a rigidification chamber of the main body portion, and in other embodiments, limit radial constriction of the rigidification chamber. In some embodiments of the invention, rigidification is accomplished by movement of fluid into a rigidification chamber and in other embodiments of the invention rigidification is accomplished by movement of fluid out of a rigidification chamber. The prosthesis includes a manually manipulable pumping arrangement to establish the necessary fluid movement for development of an erectile condition or a flaccid condition as desired.

10 Claims, 15 Drawing Sheets

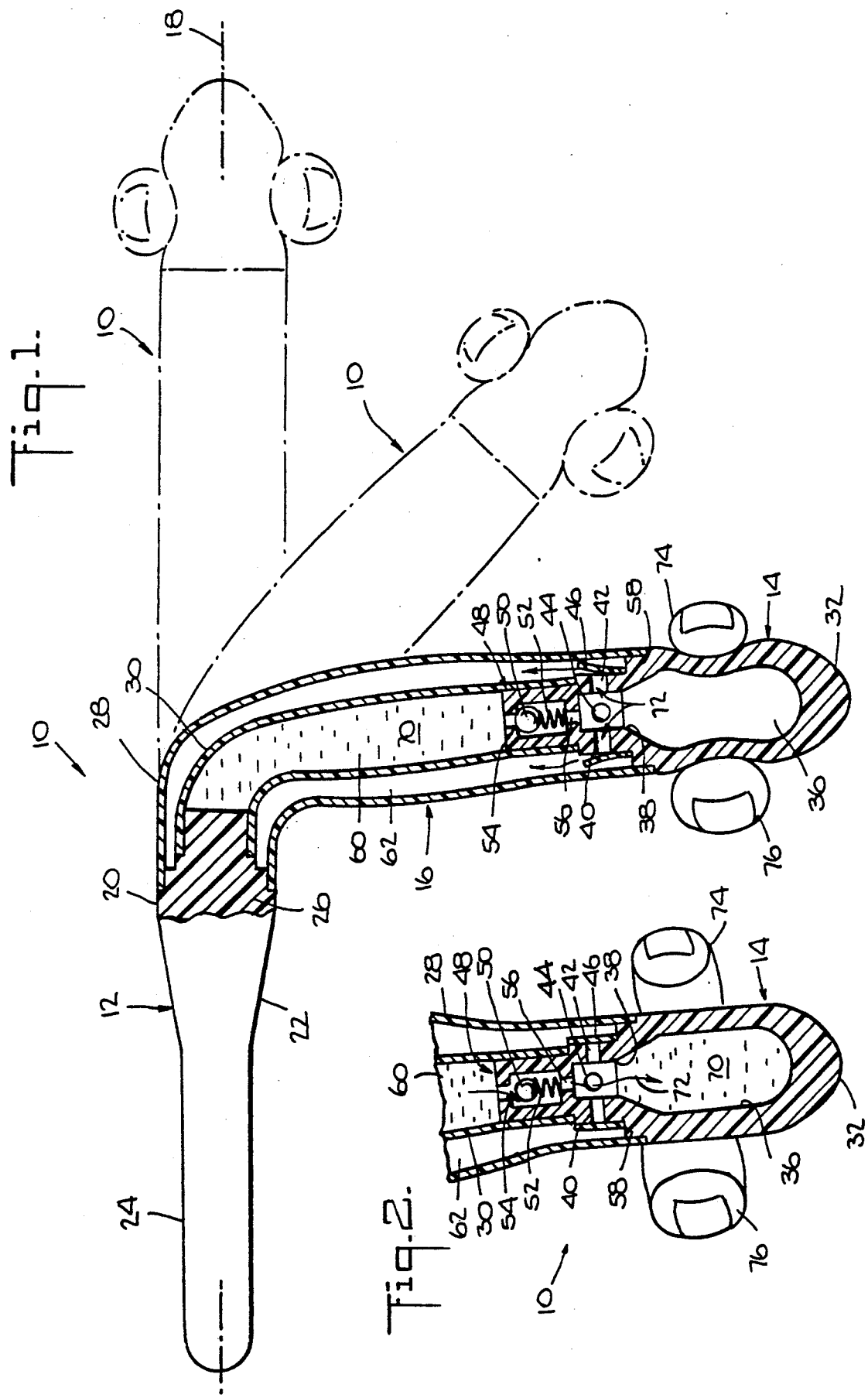

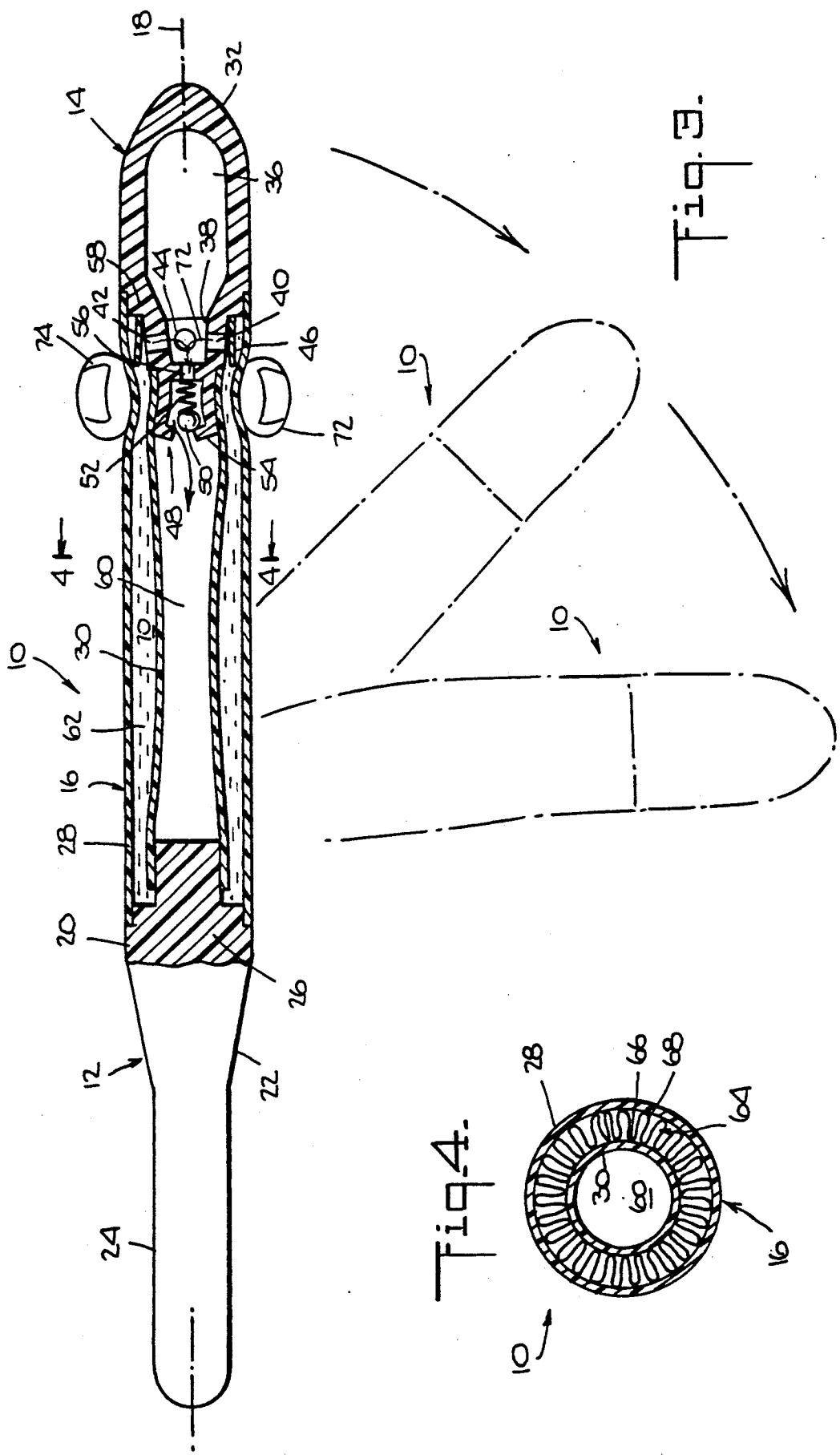

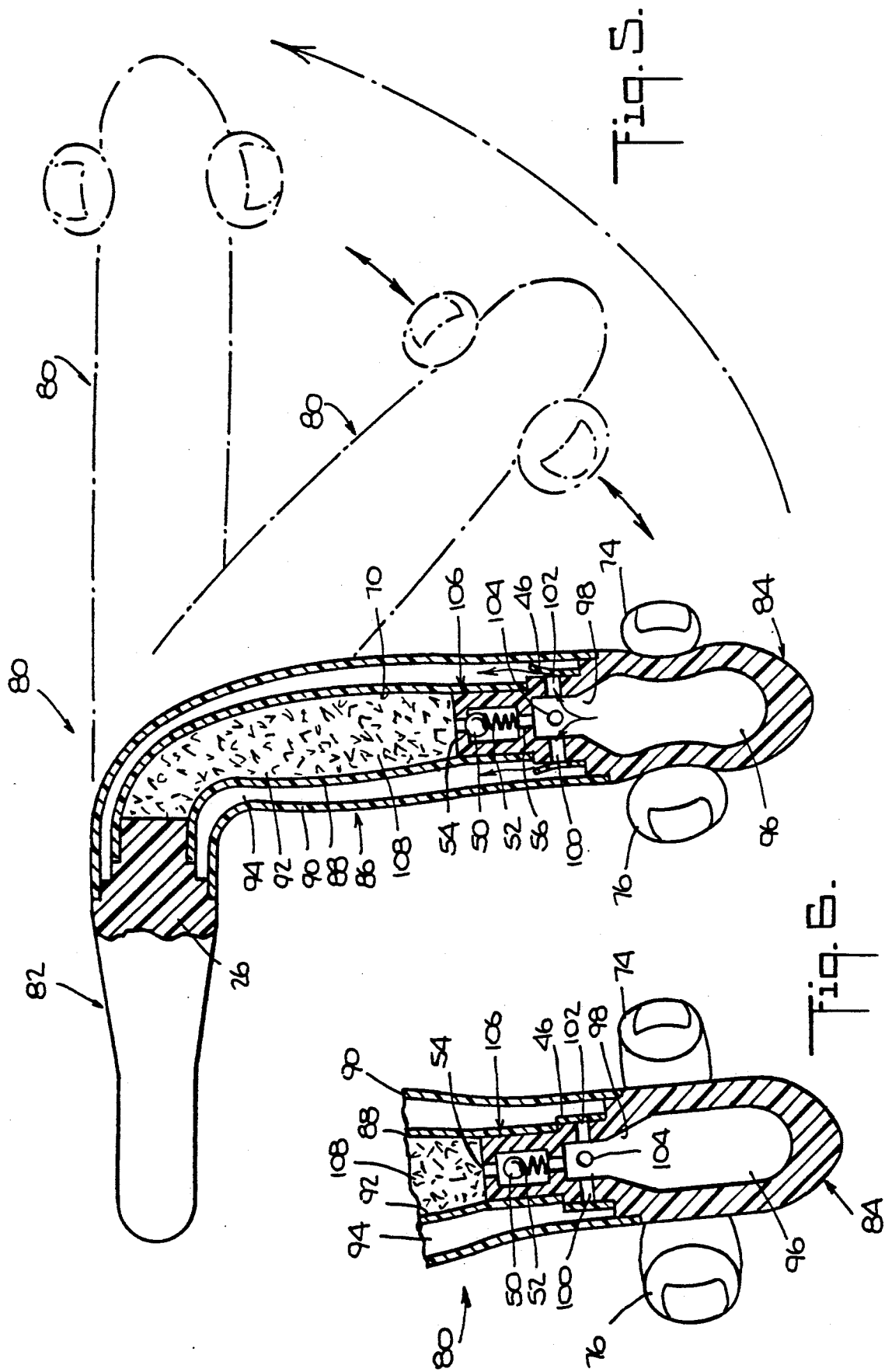

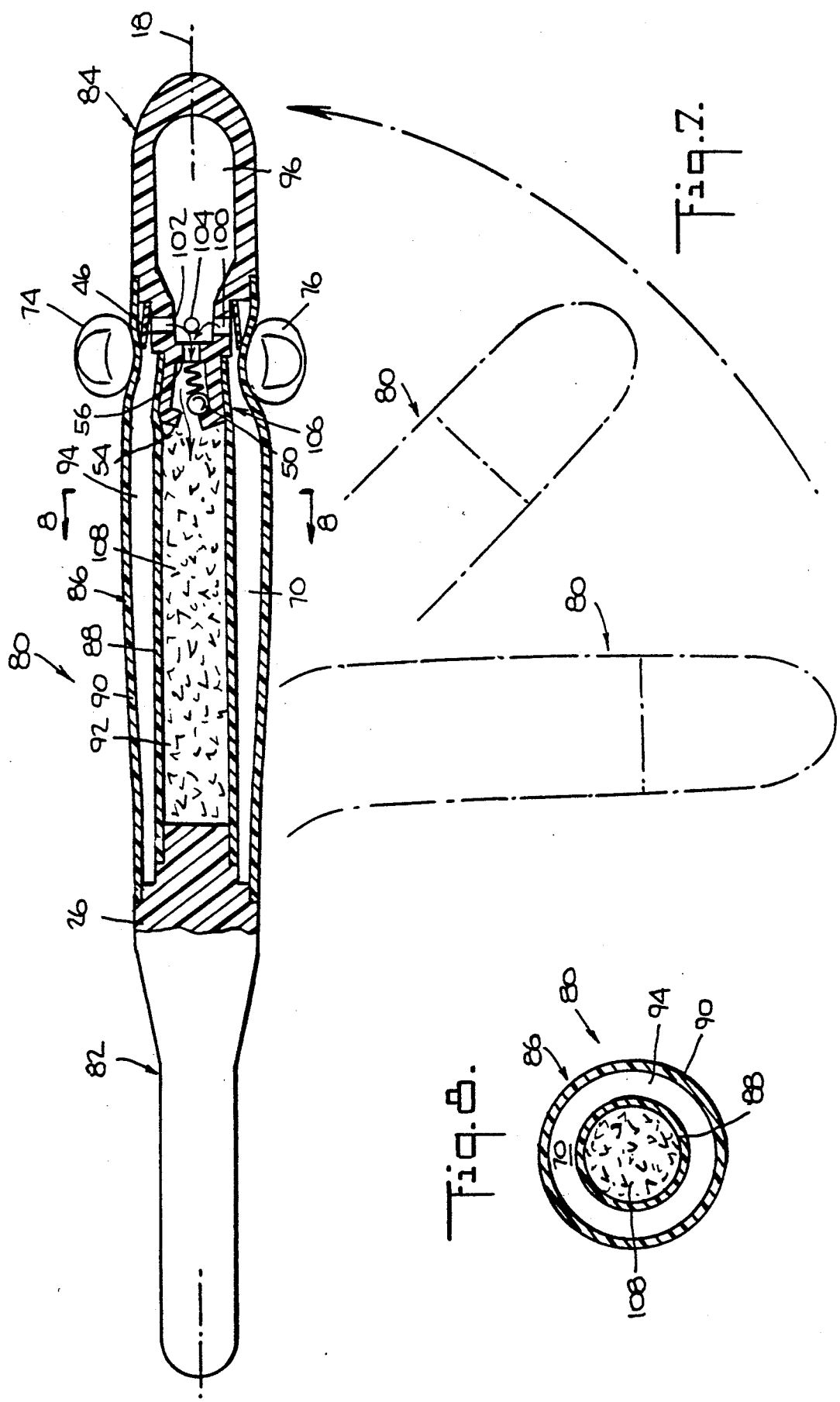

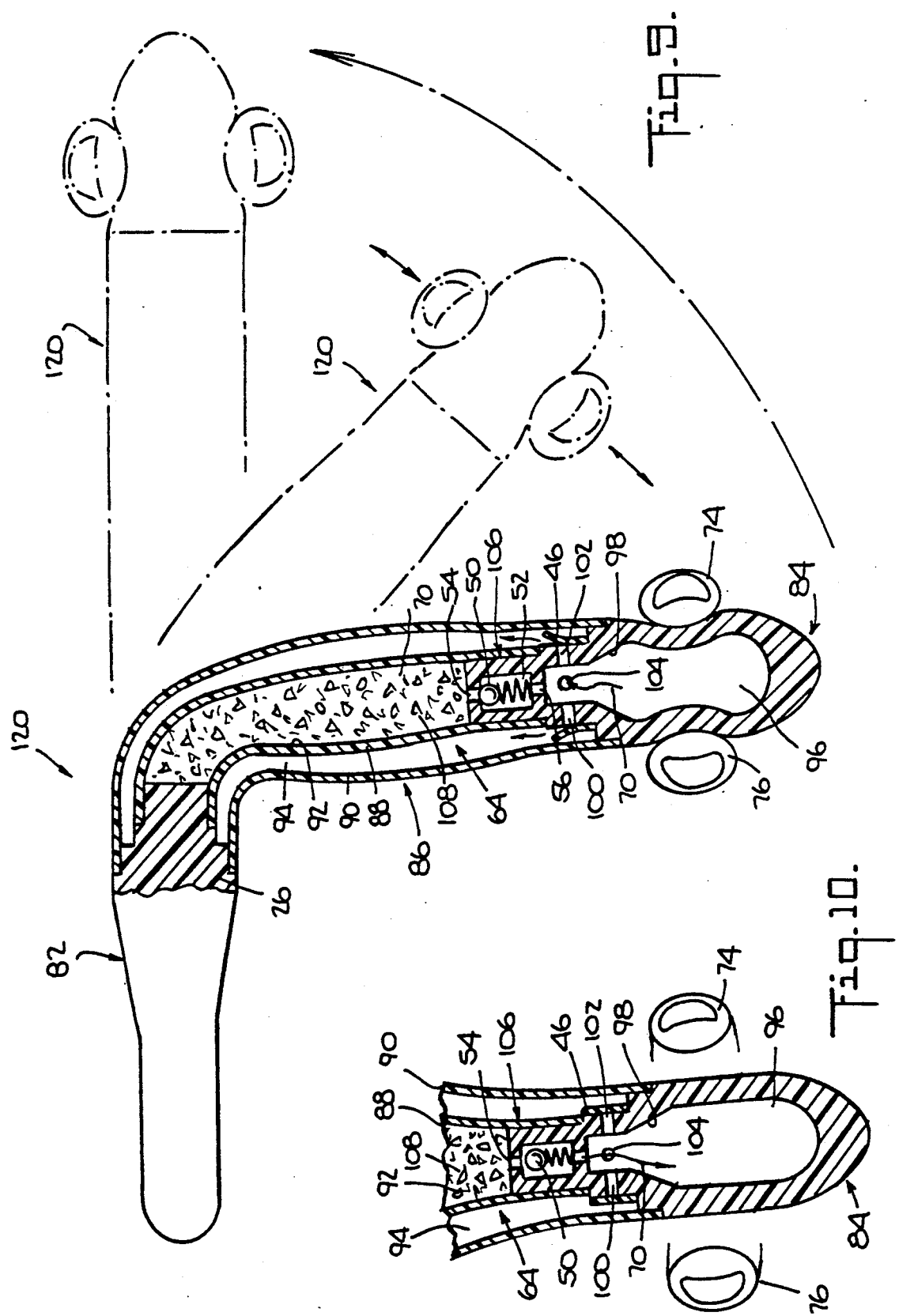

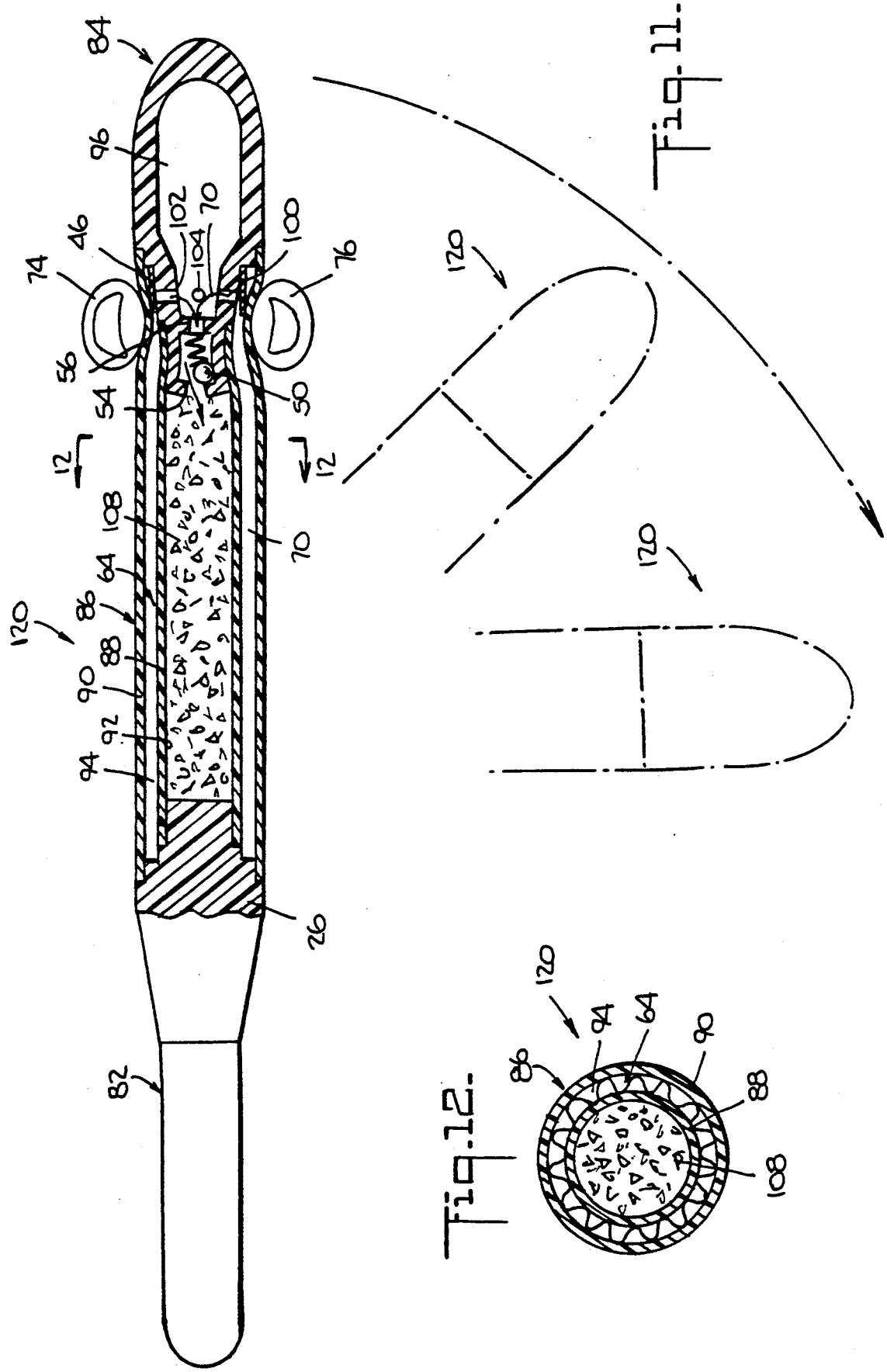

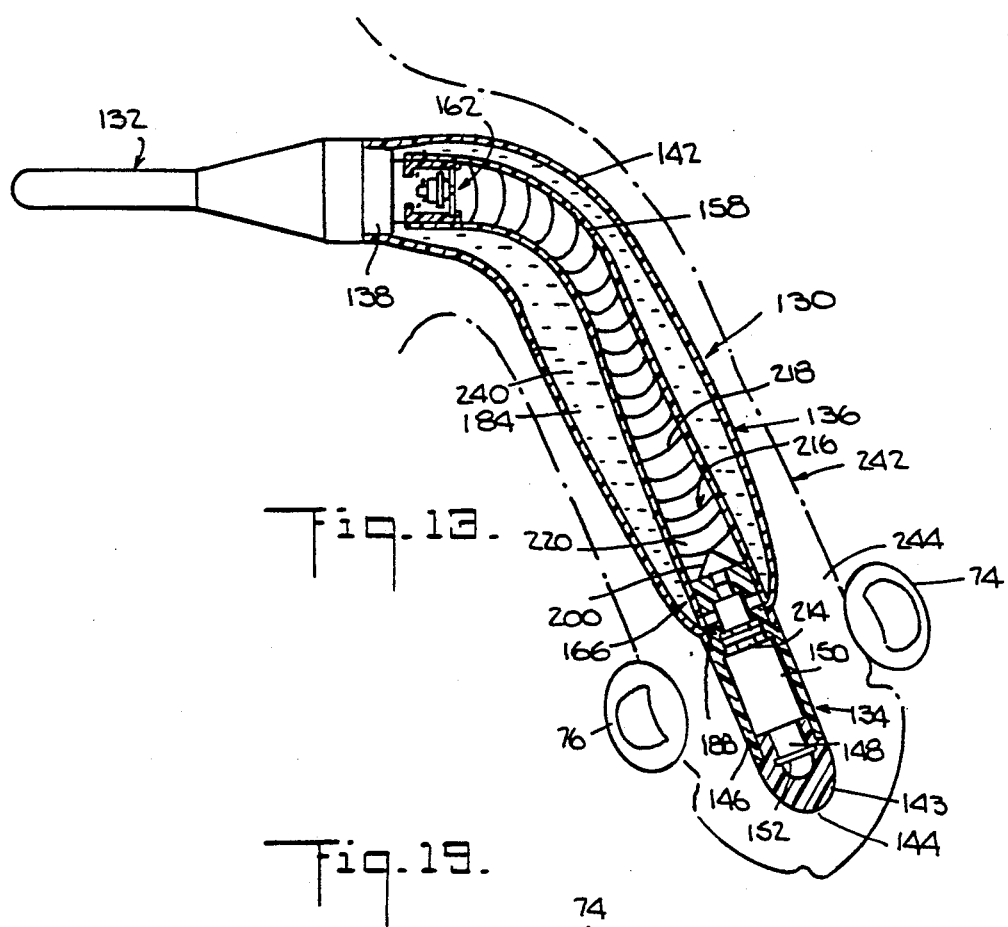
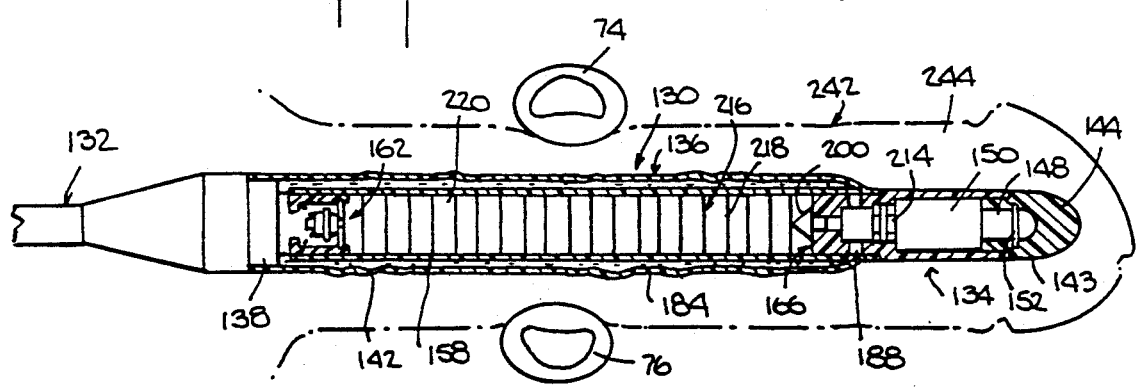
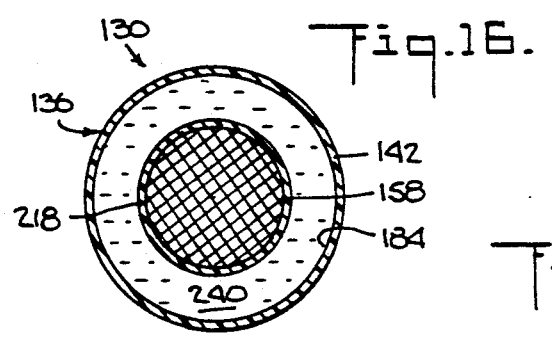
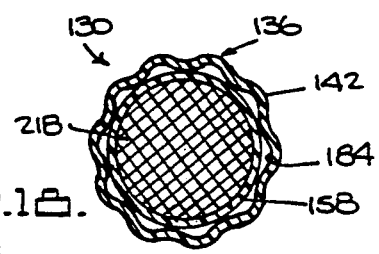

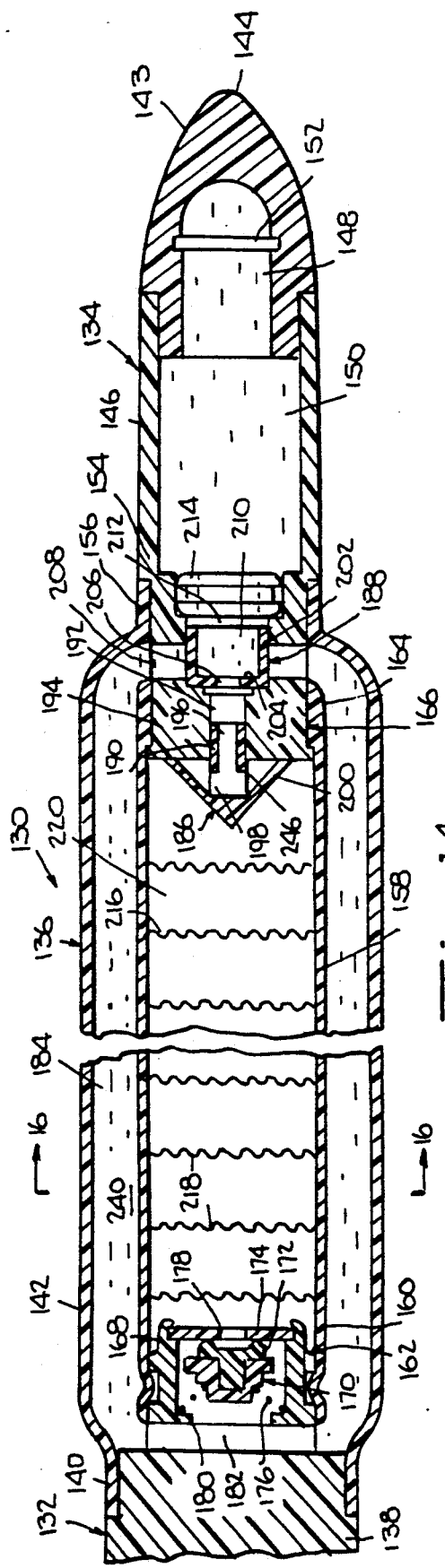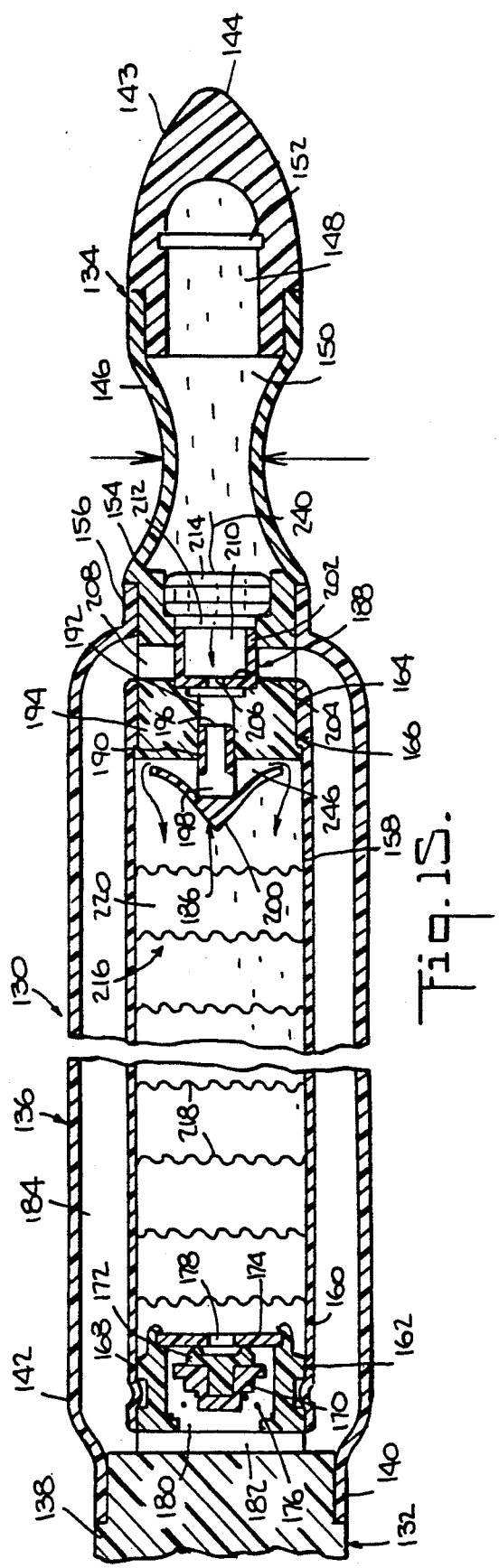

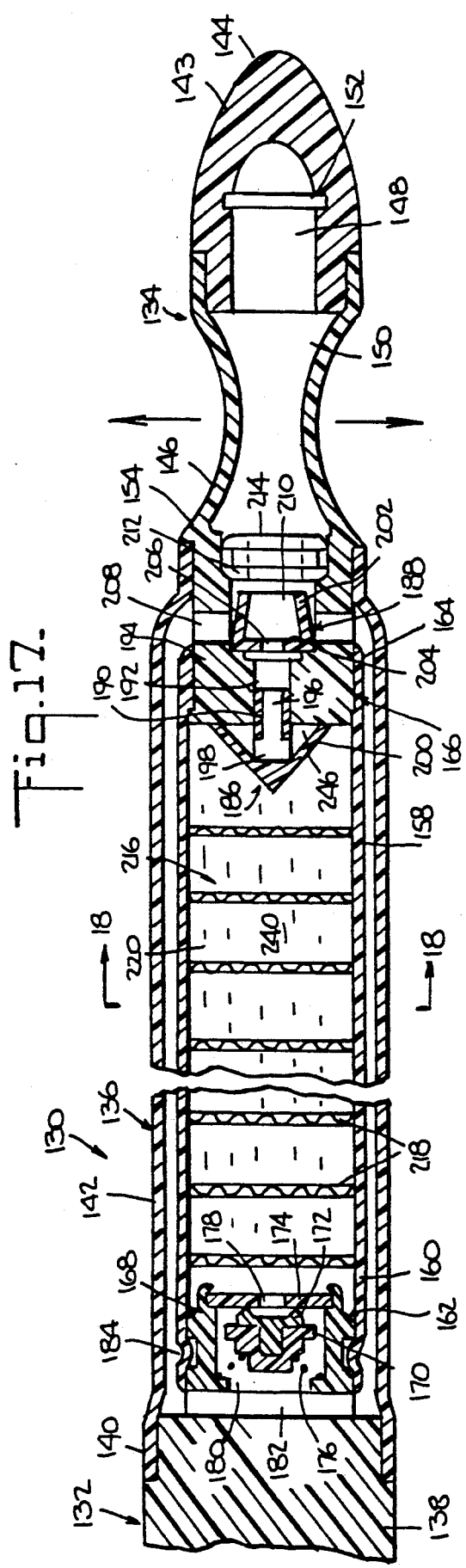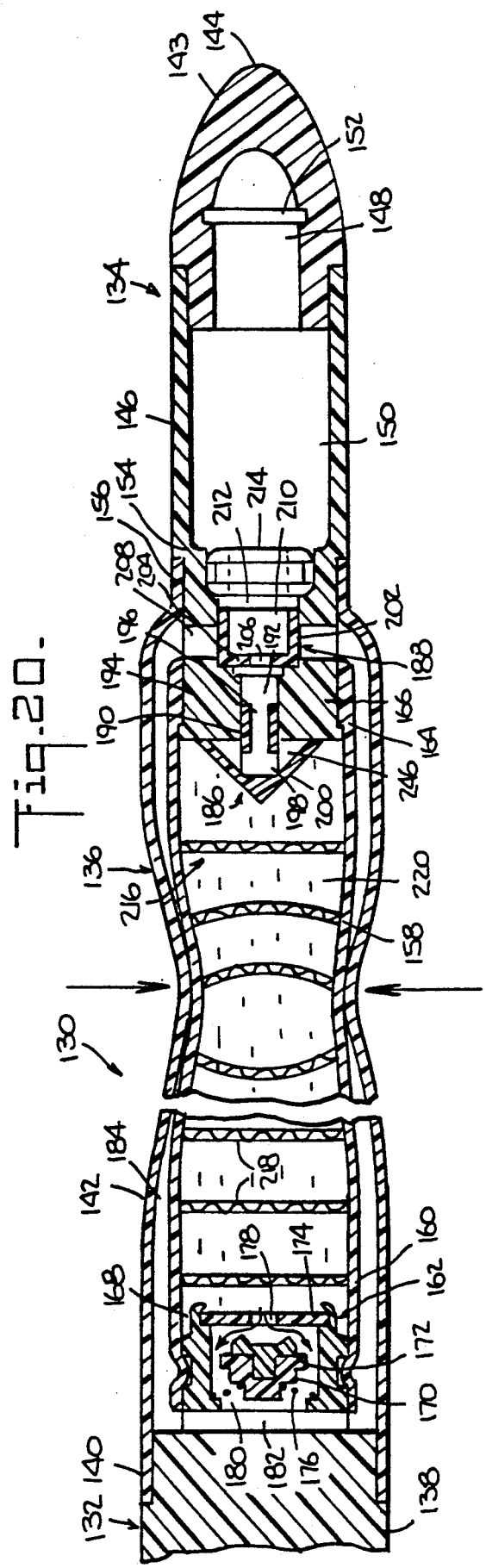

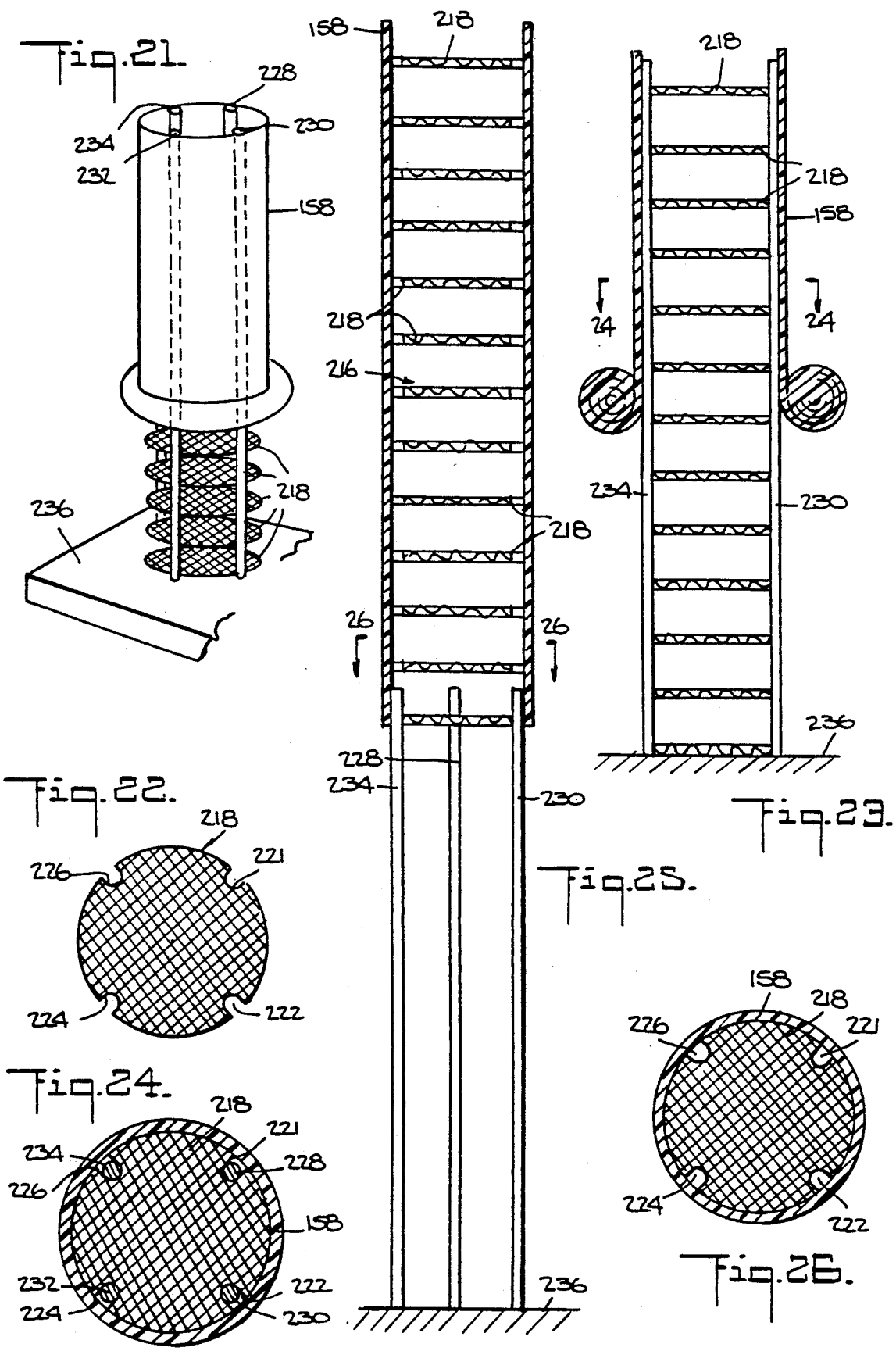

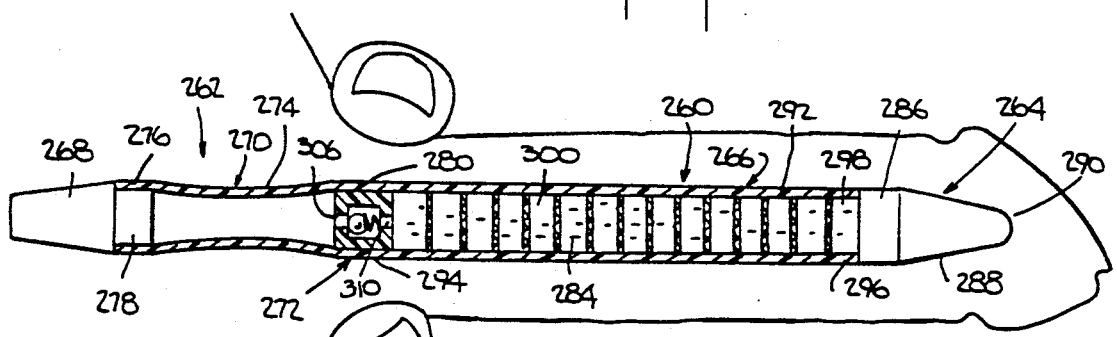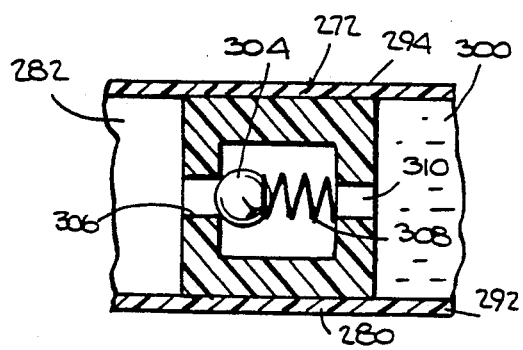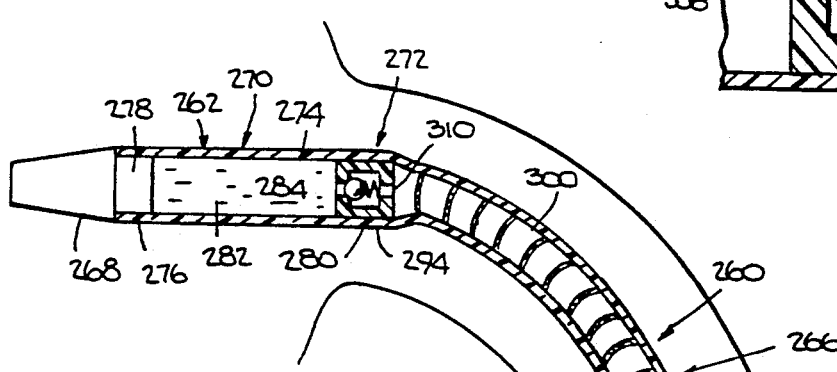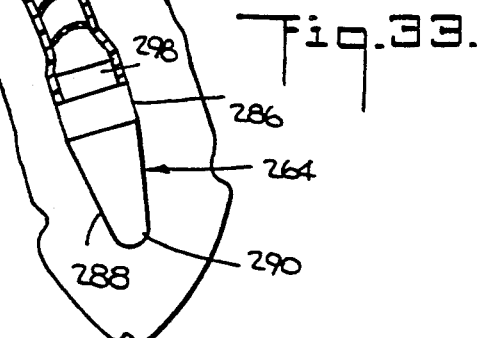

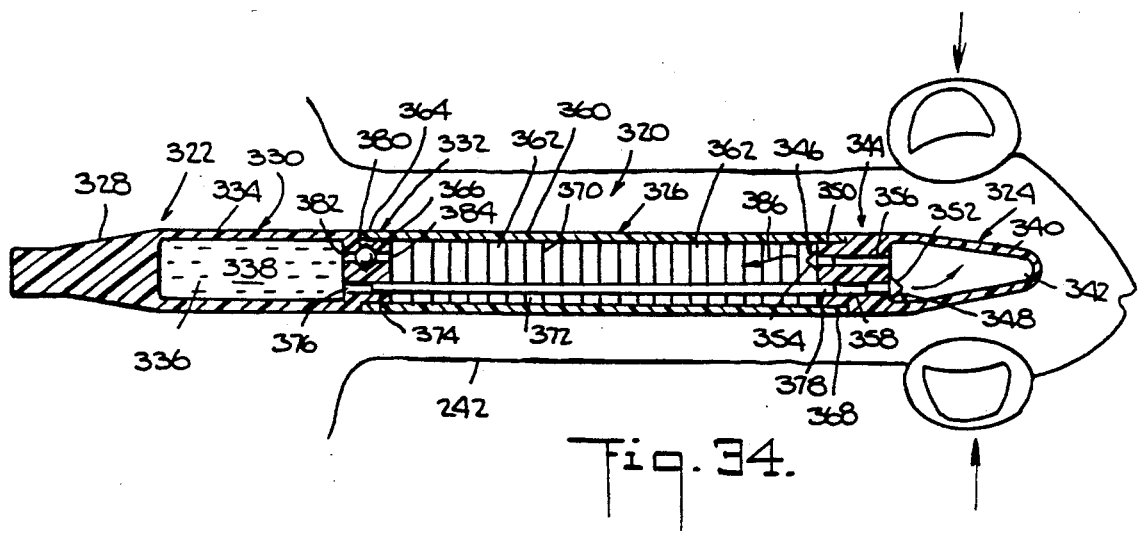
Fig. 34.
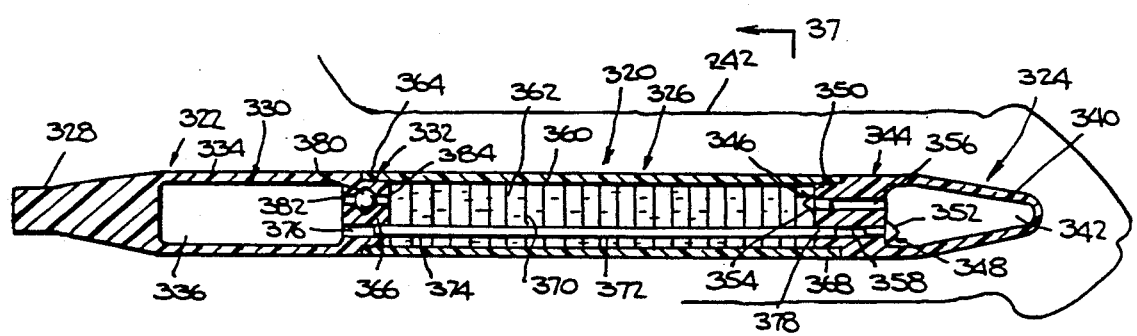
Fig. 35.
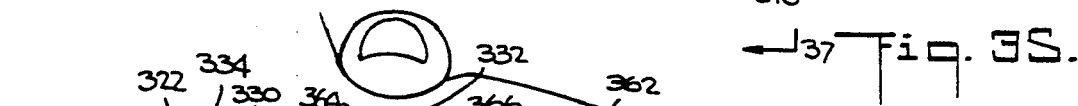
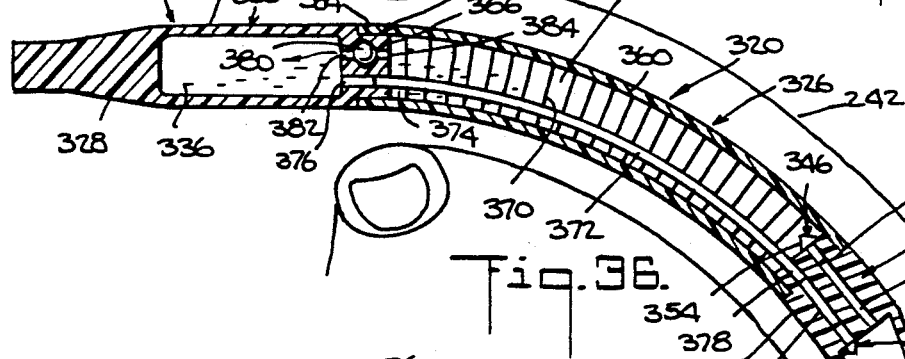
Fig. 36.
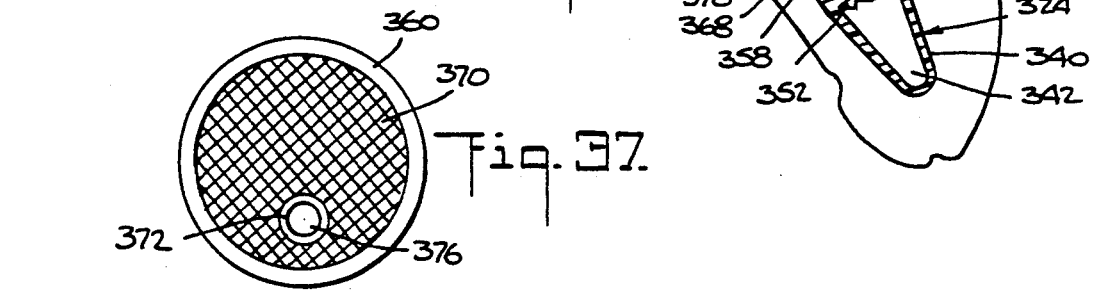
Fig. 37.

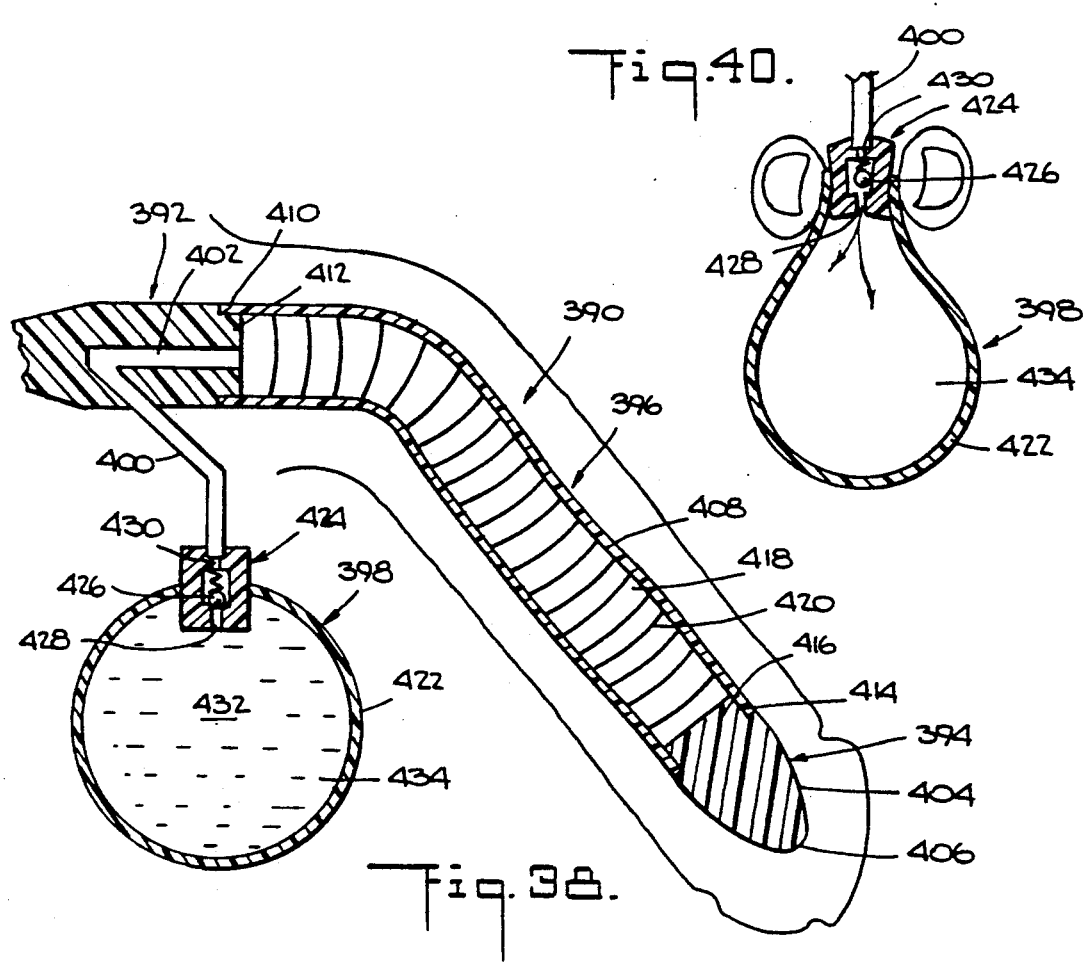
Fig. 40.
Fig. 38.
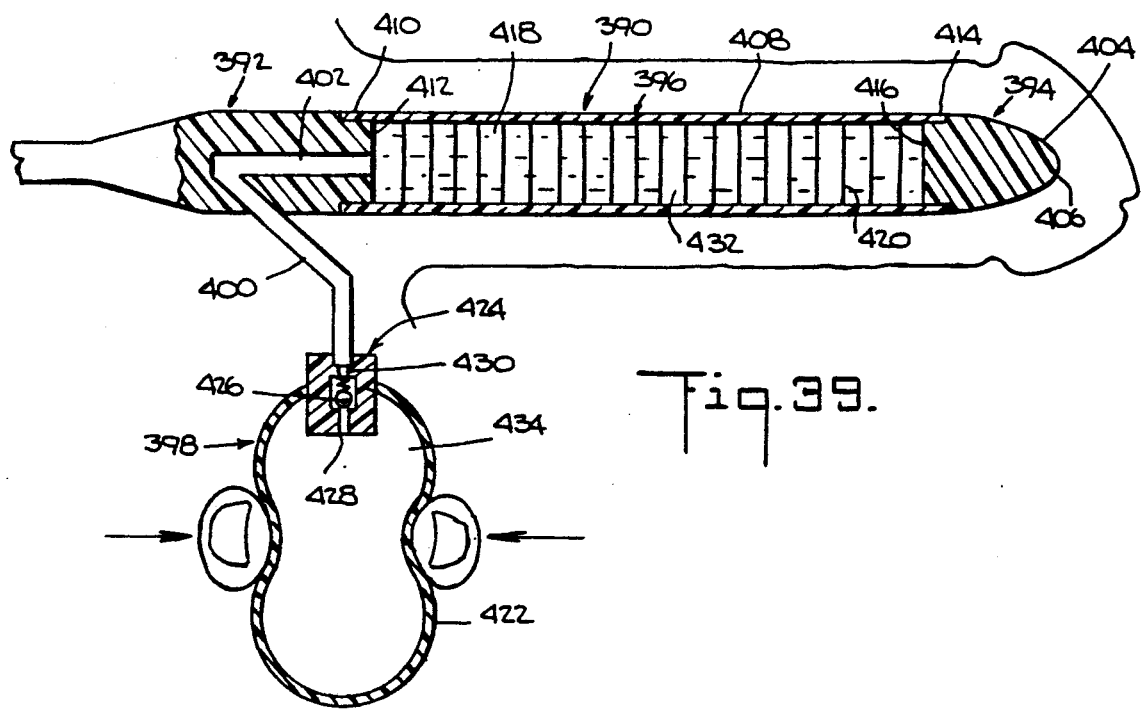
Fig. 39.

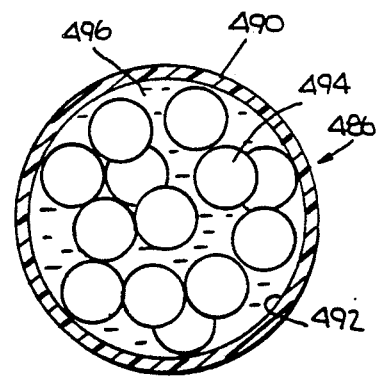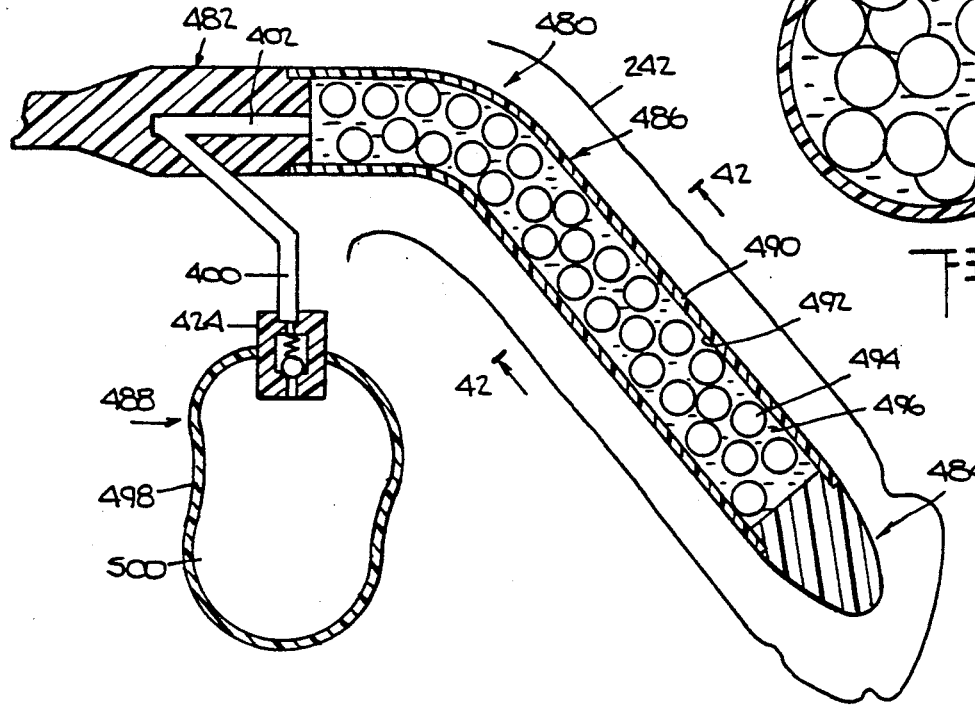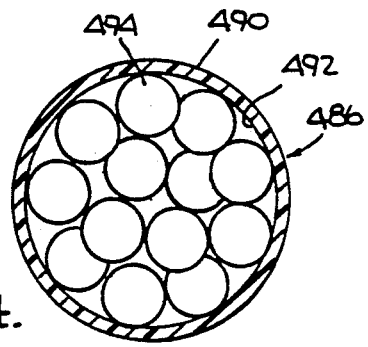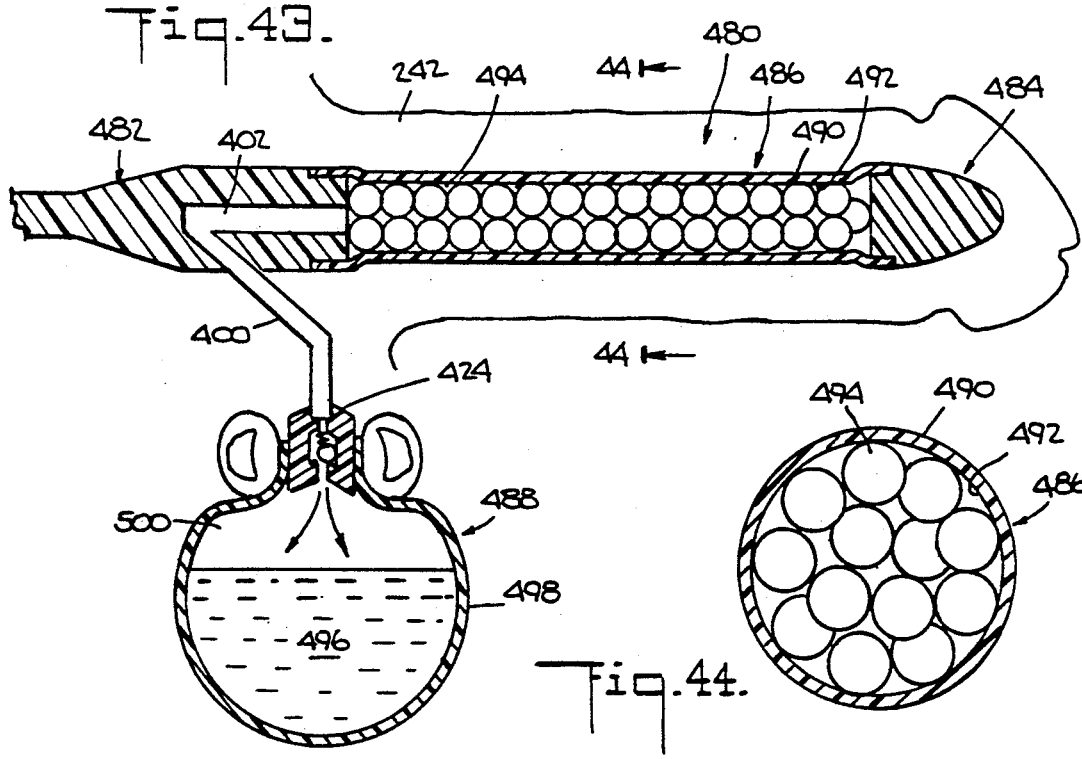

PENILE PROSTHESIS AND METHOD

This is a continuation of application Ser. No. 511,563, filed Apr. 20, 1990, now U.S. Pat. No. 5,069,201.

BACKGROUND OF THE INVENTION

This invention relates to penile erection systems for individuals who have erectile dysfunction and more particularly to a novel penile prosthesis and method for supporting the penis in an erectile position, when desired, and permitting the penis to return to a flaccid condition, when desired.

Prosthetic devices for supporting the penis in an erectile condition have long been used to compensate for erectile dysfunctions that otherwise prevent an individual from having an erection.

Generally, penile prostheses which support the penis in an erectile condition also permit the penis to assume a flaccid posture when the erectile posture is no longer desired. U.S. Pat. Nos. 3,893,465 and 4,151,840 show penile prostheses that include a relatively rigid member that supports the penis in an erectile condition and can also be bent to maintain the penis in a flaccid posture. However, the flexural stiffness of these prosthetic devices prevent the penis from having the free flexibility that is normally associated with a flaccid penis, and thus do not provide the comfort of a flaccid penis.

U.S. Pat. Nos. 4,201,202 and 4,558,693 include a combination of a flexible elongated rod surrounded by a fluid expandable chamber. However the flexible rod must be bent to place the penis in a flaccid condition and also does not provide the comfort of a flaccid penis.

Ideally a penile prosthesis should permit restoration of the penis to a flexible flaccid condition when an erectile condition is no longer desired. Fluid inflatable or expandable erectile devices such as shown in U.S. Pat. Nos. 4,009,711; 4,267,829 and 4,383,525 rely on the presence of fluid in a rigidification chamber to establish an erectile condition. The expulsion of fluid from the rigidification chamber helps establish a flaccid condition of the penis. However, such devices generally require a substantial amount of fluid and/or a substantial amount of fluid pressure within a rigidification chamber to achieve an erectile condition. As a result, the rigidification chamber wall must be reinforced as for le, by using a laminate construction such as disclosed in U.S. Pat. No. 4,267,829. The reinforced chamber wall has a predetermined stiffness that limits flexibility of the prosthesis even when the amount of pressure or fluid in the rigidification chamber is reduced. Thus, the flaccid condition of the prosthesis is limited in flexibility by the inherent stiffness of the reinforced chamber wall.

It is thus desirable to provide a penile prosthesis that can be placed in a erectile condition at a relatively low pressure and does not require flexibility-limiting reinforced walls to contain the pressure in a rigidification chamber.

As used herein, the term "flaccid condition" refers to a flexible condition of the prosthesis that corresponds to a flaccid penile condition. The term "erectile condition" as used herein refers to a rigid condition of the prosthesis that enables the prosthesis to assume a posture analogous to that of an erectile condition of the penis.

OBJECTS AND SUMMARY OF THE INVENTION

Among the several objects of the invention may be noted the provision of a novel penile prosthesis, a novel penile prosthesis that can be placed in an erectile condition upon infusion of fluid into a rigidification chamber a novel penile prosthesis that can be placed into an erectile condition upon expulsion of fluid from a rigidification chamber, a novel penile prosthesis having filler means in a rigidification chamber for determining a limit in the radial magnitude of the rigidification chamber, a novel penile prosthesis with filler means for limiting radial expansion of a rigidification chamber, a novel penile prosthesis with filler means for limiting radial constriction of a rigidification chamber, a novel penile prosthesis with filler material in a chamber to permit rigidification of the chamber upon transfer of small volumes of fluid into the chamber, a novel penile prosthesis with filler material in a chamber to permit rigidification of the chamber upon transfer of small volumes of fluid out of the chamber, and a novel method of selectively establishing a flaccid or rigid condition in a penile prosthesis.

The penile prosthesis includes proximal and distal end portions with a normally flexible main body portion adjoining the proximal and distal end portions. The main body portion includes at least one sleeve that defines a sleeve chamber that includes filler material for limiting change in the radial dimension of the chamber beyond a predetermined limit.

In some embodiments of the invention the filler material is arranged to limit radial expansion of the chamber and in other embodiments of the invention the filler material is arranged to limit radial constriction or collapse of the chamber.

In the embodiments with filler material for limiting radial expansion of the chamber, rigidification of the chamber and consequential rigidification of the prosthesis is accomplished by filling the chamber to an expansion limit condition. The fluid needed to reach the expansion limit condition is less than the volume of the chamber by an amount substantially equivalent to the volume of filler material. The filler material for limiting radial expansion of the chamber can include webbing, which in some embodiments is axially elongated and radially corrugated, and in other embodiments is in the form of disks.

In several embodiments of the invention which incorporate filler material for limiting radial constriction of the chamber, rigidification of the prosthesis is accomplished by expelling fluid from the chamber to cause the chamber to constrict to a constriction limit condition. The amount of fluid expelled from the chamber to cause the chamber to reach the constriction limit condition is less than the volume of the chamber by an amount substantially equivalent to the volume of filler material. The filler material for limiting constriction of the chamber can include an aggregation of fibers, strands, beads, spheres, and other objects of regular or irregular shape which occupy space in the chamber.

When fluid is present in the chamber, the chamber volume is maximized to permit relative movement between the individual particles or members of the aggregate. When fluid is removed from the chamber containing the aggregate, fluid pressure in the chamber is reduced, and the chamber walls constrict or collapse around the aggregate to bind the aggregate and prevent any relative movement between the individual particles or members of the aggregate. Thus a rigidification condition is established in the chamber when the volume of fluid in the chamber is minimized.

In all embodiments of the invention the development of a rigidification condition in any of the chambers of the main body portion will place the prosthesis in a substantially inflexible rigid condition that will support the penis in an erectile condition.

In some embodiments of the invention the main body portion includes one sleeve chamber and in other embodiments of the invention the main body portion of the prosthesis includes two sleeve chambers.

Pumping means for pumping fluid into or out of the sleeve chambers to accomplish rigidification of the prosthesis can be provided at a proximal end of the prosthesis in some embodiments, and at a distal end of the prosthesis in another embodiment. In further embodiments, the pumping means can be provided at a remote location from the pendulous portion of the prosthesis as, for example, in the scrotal sac.

In all embodiments of the invention the development of a flaccid condition or an erectile condition is accomplished through manual manipulation of the prosthesis through the penile tissue or through the scrotal sac. Thus the user can achieve a flaccid or erectile condition as desired.

The invention accordingly comprises the constructions and method hereinafter described, the scope of the invention being indicated in the claims.

DESCRIPTION OF THE DRAWINGS

In the accompanying drawings,

FIG. 1 is a simplified schematic view of a penile prosthesis, partly shown in section, incorporating one embodiment of the invention and showing a transitioning of the penile prosthesis from a position corresponding to a condition of penile flaccidity (hereinafter referred to as "flaccid condition"), to a position corresponding to an erectile condition of the penis, (hereinafter referred to as "erectile condition") during a pumping operation;

FIG. 2 is a fragmentary detail thereof, similar to FIG. 1, during another stage of the pumping operation;

FIG. 3 is a simplified schematic view thereof, partly shown in section, in an erectile condition and showing transitioning of the prosthesis from the erectile condition to a flaccid condition;

FIG. 4 is a sectional view thereof taken on the line 4—4 of FIG. 3;

FIG. 5 is a simplified schematic view, partly shown in section, of another embodiment of the invention showing the transitioning of the prosthesis from a flaccid condition to an erectile condition, during a pumping operation;

FIG. 6 is a fragmentary detail thereof, similar to FIG. 5, during another stage of the pumping operation;

FIG. 7 is a simplified schematic view thereof, partly shown in section, in an erectile condition and showing transitioning of the prosthesis from the erectile condition to a flaccid condition;

FIG. 8 is a sectional view taken on the line 8—8 of FIG. 7;

FIG. 9 is a simplified schematic view, partly shown in section, of another embodiment of the invention, showing the transitioning of the prosthesis from a flaccid condition to the erectile condition during a pumping operation;

FIG. 10 is a fragmentary detail thereof similar to FIG. 9, during another stage of the pumping operation;

FIG. 11 is a simplified schematic view thereof, partly shown in section, in an erectile condition and showing transitioning of the prosthesis from the erectile condition to a flaccid condition;

FIG. 12 is a sectional view taken on the line 12—12 of FIG. 11.

FIG. 13 is a simplified schematic view, partly shown in section, of another embodiment of the invention wherein the prosthesis is in a flaccid condition.

FIG. 14 is an enlarged fragmentary detail thereof, partly shown in section, in a flaccid condition;

FIG. 15 is a view similar to FIG. 14 during a pumping operation for placing the prosthesis in an erectile condition;

FIG. 16 is a sectional view taken on the line 16—16 of FIG. 14;

FIG. 17 is a view similar to FIG. 15 during another stage of the pumping operation;

FIG. 18 is a sectional view taken on the line 18—18 of FIG. 17;

FIG. 19 is a view similar to FIG. 13 showing the prosthesis in an erectile condition and being manipulated for transitioning to a flaccid condition;

FIG. 20 is an enlarged detailed sectional view thereof after being manipulated as shown in FIG. 19;

FIGS. 21-26 are detail views showing a subassembly thereof;

FIG. 30 is an enlarged detailed sectional view showing a valve arrangement thereof;

FIG. 31 is a simplified schematic view thereof, partly shown in section, during manipulation to transition the prosthesis from the erectile condition to the flaccid condition;

FIG. 32 is similar to FIG. 30 showing valve distortion after being manipulated as shown in FIG. 31;

FIG. 33 is a view similar to FIG. 31 showing the prosthesis in a flaccid condition;

FIG. 34 is a simplified schematic view, partly shown in section, of another embodiment of the invention, during a pumping operation to establish an erectile condition;

FIG. 35 is a view similar to FIG. 34 showing the prosthesis in an erectile condition;

FIG. 36 is a view similar to FIG. 35 showing the prosthesis being manipulated for transitioning from the erectile condition to a flaccid condition;

FIG. 37 is an enlarged sectional view thereof taken on the line 37—37 of FIG. 35;

FIG. 38 is a simplified schematic view, partly shown in section, of another embodiment of the penile prosthesis in a flaccid condition;

FIG. 39 is a view similar to FIG. 38 showing the prosthesis during a pumping operation for placing the prosthesis in an erectile condition;

FIG. 40 is a fragmentary detail thereof showing valve distortion during manipulation of the prosthesis for transitioning the prosthesis from the erectile condition of FIG. 39 to the flaccid condition of FIG. 38;

FIG. 41 is a simplified schematic view, partly shown in section, of another embodiment of the invention, in a flaccid condition;

FIG. 42 is an enlarged sectional view thereof taken on the line 42—42 of FIG. 41;

FIG. 43 is a view similar to FIG. 41 showing the prosthesis in an erectile condition; and, FIG. 44 is a sectional view taken on the line 44—44 of FIG. 43.

Corresponding reference characters indicate corresponding parts throughout the several views of the drawings.

DETAILED DESCRIPTION OF THE INVENTION

Figure 27:
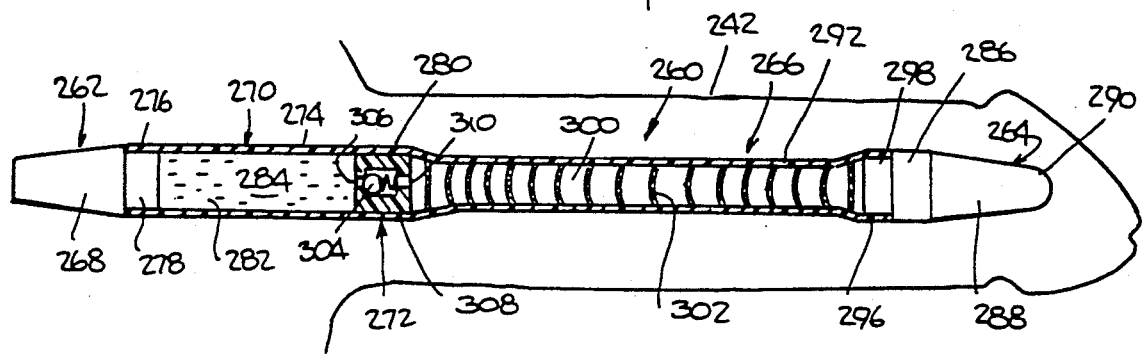
FIG. 27 is a simplified schematic view, partly shown in section, of another embodiment of the invention, in a flaccid condition.

A penile prosthesis incorporating one embodiment of the invention is generally indicated by the reference number 10 in FIG. 1.

The prosthesis 10 comprises a proximal end portion 12, a distal end portion 14, and a main body portion 16 extending from the proximal end portion 12 to the distal end portion 14.

The prosthesis 10 has a predetermined longitudinal extent along a longitudinal axis 18, as shown dotted in FIG. 1. Further references to the term axis or axial are intended to refer or relate to the longitudinal axis 18.

The proximal end portion 12, which is formed of a relatively firm medical grade elastomer such as silicone, includes a generally cylindrical section 20, a tapered conical section 22 and a rod-like mounting section 24 that extends from the tapered section 22.

The cylindrical section 20 includes a stepped end portion 26 that is joined to an outer sleeve 28 and a coaxial inner sleeve 30 of the main body portion 16. The sleeves 28 and 30 are flexible but nondistensible and can be formed of a suitable biocompatible material such as Dacron polyester.

The distal end portion 14, which is also formed of a relatively firm medical grade elastomer such as silicone is substantially cylindrical in shape with a conically tapered, gently curved free end 32. A pump chamber 36 is defined within the distal end portion 14. The chamber 36 has a proximally directed neck portion 38 with radially distributed openings such as 40, 42 and 44. An annular closure flap 46 normally closes the openings 40, 42 and 44 to prevent fluid flow into the chamber 36 through the openings 40, 42 and 44.

A valve 48 extends from the neck portion 38 of the chamber 36 and includes a ball 50 normally biased by a spring 52 against a valve seat 54. The valve 48 also includes an opening 56 disposed opposite the valve seat 54. The opening 56 is communicable with the pump chamber 36 through the neck portion 38.

The outer sleeve 28 of the main body portion 16 is joined to a stepped portion 58 of the distal end 14, and the coaxial inner sleeve 30 is joined to the periphery of the valve 48.

A generally cylindrical sleeve chamber 60 is defined by the inner sleeve 30 and a generally annular outer sleeve chamber 62 is defined between the outer sleeve 28 and the inner sleeve 30.

Filler means provided in the outer sleeve chamber 62 include a flexible, nondistensible corrugated webbing 64 as most clearly shown in FIG. 4. The webbing 64, which can be formed of Dacron mesh, is elongated in the longitudinal axial direction. The webbing 64 has a radially inner extremity 66 joined to the inner sleeve 30 and a radially outer extremity 68 joined to the outer sleeve 28.

The prosthesis 10 is implanted in the penis (not shown) in any suitable known manner, preferably between or within one of the corpus cavernosum of the penis. The proximal portion 12 is preferably positioned in the root segment of the corpus cavernosum with the main body portion 16 disposed within the pendulous section of the penis. The distal end portion 14 is adapted to be positioned under the glans of the penis.

A predetermined amount of fluid 70 such as isotonic saline is provided in the inner chamber 60 of the inner sleeve 30. The amount of fluid 70 used in the prosthesis 10 is predetermined to ensure that there is sufficient flexibility of the chamber 60 to allow the penis to assume a flaccid condition even if all the fluid 70 in the prosthesis 10 is within the inner sleeve chamber 60.

The outer sleeve chamber 62 is of less volume than the inner sleeve chamber 60. For example, for a particular individual requirement the inner sleeve chamber can be approximately 5 to 8 ccs in volume, whereas the outer sleeve chamber can be approximately 2.5 to 4 ccs in volume, and the pump chamber 36 is approximately 0.5 to 2 ccs in volume for a prosthesis having an axial sleeve length of approximately 10 to 12 cms.

When it is desired to place the prosthesis 10 in an erectile condition, the distal end portion 14 of the prosthesis is gently compressed by the fingers 74 and 76 to correspondingly compress the pump chamber 36. Although FIGS. 1-12 do not show the penis, it is to be understood that manipulation of the prostheses as described herein is through the penile tissue.

During compression of the pump chamber 36 the valve 48 remains in its normally closed condition with the ball 50 against the valve seat 54 under the influence of the biasing spring 52. Compression of the pump chamber 36 exerts a pressure force on the annular closure flap 46 through the openings 40, 42 and 44 as indicated by the arrows 72 in FIG. 1. Thus compression of the distal portion 14 establishes communication between the pump chamber 36 and the outer sleeve chamber 62 through the openings 40, 42 and 44.

When the pump chamber 36 is decompressed as indicated by the spread fingers 74 and 76 in FIG. 2, the pump chamber 36 is permitted to expand to its normal volume, thereby drawing the fluid 70 into the pump chamber 36 from the inner sleeve chamber 60. The drawn in fluid 70 overcomes the biasing force of the valve spring 52 against the ball 50, thereby unseating the ball 50. The fluid 70 thus flows through the valve seat 54, past the valve opening 56, into the neck portion 38, for accumulation in the pump chamber 36.

A sequential compression of the pump chamber 36 in the manner previously described causes the fluid 70 in the pump chamber 36, as shown in FIG. 2, to be forced through the openings 40, 42 and 44 into the annular outer sleeve chamber 62.

As the fluid 70 is pumped into the annular outer sleeve chamber 62 and fills such chamber to capacity, the corrugated webbing 64 (FIG. 4) prevents the outer sleeve 28 from expanding beyond a predetermined radial magnitude relative to the inner sleeve 30. The chamber 62 thus has a substantially predetermined maximum volume or capacity.

The fluid 70 that is pumped into the chamber 62 to expand the chamber to its maximum volume places the corrugated webbing 64 under tension and causes rigidification of the chamber 62 when such chamber is filled to capacity.

Pressure buildup in the chamber 62 is accomplished in a relatively quick fashion after the chamber is filled to capacity because the chamber 62 is essentially nonexpandible beyond a predetermined radial magnitude determined by the inner and outer extremities 66 and 68 of the webbing 64. Furthermore, a relatively small amount of fluid 70 is needed to fill the chamber 62 since the webbing 64 functions as a filler material as well as a means for limiting change in the radial dimension of the chamber 62 beyond the predetermined radial magnitude.

It will be noted that during the pumping of the fluid 70 from the pump chamber 36 into the outer sleeve chamber 62, the biasing spring 52 urges the ball 50 into its normally seated position on the valve seat 54. The force of the biasing spring 52 on the ball 50 is also supplemented by the pressure of the fluid 70 being pumped from the pump chamber 36 into the outer sleeve chamber 62.

The outer sleeve chamber 62 thus functions as a rigidification chamber for the prosthesis 10 enabling the prosthesis to be placed in an erectile condition as shown in dotted outline in FIG. 1.

When it is desired to have the penis assume a flaccid condition, pressure is applied to the prosthesis 10 at the valve 48 as shown by the fingers 74 and 76 in FIG. 3. Pressure applied to the valve 48 as shown in FIG. 3 distorts the configuration of the valve 48 and the neck portion 38. Thus the seal between the annular closure flap 46 and the openings 40, 42 and 44 is broken, and the valve seat 54 is sufficiently distorted such that the ball 50 can no longer seal against the valve seat 54. The valve 48 is thus held open when distorted.

In this manner the fluid 70 is permitted to flow from the outer sleeve chamber 62 through the openings 40, 42 and 44, into the pump chamber 36 for passage through the opening 56, past the valve ball 50, through the valve seat 54 and into the inner sleeve chamber 60. Movement of the fluid 70 from the outer sleeve chamber 62 back into the inner sleeve chamber 60 is further facilitated by gentle bending or manual compression of the main body portion 16 to help force the fluid 70 from the outer sleeve chamber 62 into the pump chamber 36.

Another embodiment of the penile prosthesis is generally indicated by the reference number 80 in FIGS. 5-8. The prosthesis 80 includes a proximal end portion 82, a distal end portion 84, and a main body portion 86. The main body portion 86 includes inner and outer sleeves 88 and 90 that respectively define an inner sleeve chamber 92 and an outer sleeve chamber 94. Unless otherwise stated, the structure of the prosthesis 80 is similar to that of the prosthesis 10.

The distal end portion 84 includes a pump chamber 96, a neck portion 98 with openings 100, 102, 104, and a valve 106, all of which are structurally similar to corresponding structure in the prosthesis 10.

An aggregate of nonsoluble filler material 108 is provided in the inner sleeve chamber 92. The filler material 108 can be solid or flexible insoluble members, made of any suitable material such as metal or plastic, of regular or irregular shape such as polyhedrons, disks, rings, cylinders, rods, spheres, fibers, which are preshaped or complex, bubbles, fluid-filled balloons, liquid filled spheres, or BBs, etc. Specific examples of filler material can be silica, aluminum oxide, cellulose, carbon, titanium, crystalline salt or other suitable crystalline material.

A predetermined volume of fluid 70 is provided in the inner sleeve chamber 92 which does not pressurize the chamber 92 and permits flexibility and bending of the chamber 92 with the aggregate 108 in a manner which corresponds to a flaccid condition of a penis.

For example, for an inner sleeve chamber of approximately 5 to 9 ccs capacity, the aggregate of material 108 would occupy approximately 4 to 8 ccs and the amount of fluid 70 in the chamber 92 would occupy approximately 1 to 2 ccs.

It should be noted that in the prosthesis 80 the outer sleeve chamber 94 is free of any filler material or webbing.

In use, the prosthesis 80 is implanted in the penis in a known manner similar to that previously described for the prosthesis 10. When the penis (not shown) is in a flaccid condition, the aggregate of filler material 108 and the fluid 70 in the inner sleeve chamber 92 permit relative shifting movement of individual members of the aggregate 108 relative to each other.

When an erectile condition is desired, the pump chamber 96 is compressed in a manner similar to that previously described for the prosthesis 10. Compression of the pump chamber 96 causes any fluid 70 therein to pass through the openings 100, 102 and 104 into the outer sleeve chamber 94. A sequential decompression of the distal end portion 84 allows the pump chamber 96 to expand to its normal volume. During such expansion fluid from the inner sleeve chamber 92 is drawn into the pump chamber 96 through the valve 106 in a manner similar to that previously described for the prosthesis 10.

Sequential compression of the distal end portion 84 to compress the pump chamber 96 forces the fluid 70 in the pump chamber 96 into the outer sleeve chamber 94 while the inner sleeve chamber 92 is sealed by the valve 106.

As the fluid 70 is drawn or pumped from the inner sleeve chamber 92 and pumped into the outer sleeve chamber 94, the inner sleeve 88 constricts or collapses around the aggregate of filler 108 binding such aggregate in a close, compact relationship to prevent any relative movement between the composite parts of the aggregate 108.

The aggregate material 108 is thus tightly bound by the sleeve 88 such that the chamber 92 becomes substantially rigid. Since the sleeve 88 is substantially nondistensible and has a uniform axial length, the constriction of the sleeve 88 around the aggregate 108 enables the prosthesis 80 to constrict from the flaccid condition shown in FIG. 5 to an erectile condition shown in dotted outline in FIG. 5, and in section in FIG. 7.

It will be noted that the prosthesis 80 is manipulated to a desired erectile posture and then fluid evacuation is obtained. The prosthesis, during fluid evacuation, assumes the manipulated erectile posture. Thus when the prosthesis 80 rigidifies it maintains the erectile posture and after rigidification is completed the prosthesis sustains the erectile posture without outside manipulative support.

It will be noted that the amount of the aggregate of filler material 108 in the inner sleeve chamber 92 is predetermined to ensure that substantial elimination of fluid 70 from the inner sleeve chamber 92 results in rigidification of the inner sleeve chamber 92. Thus, as the fluid 70 is withdrawn from the inner sleeve chamber 92, the prosthesis 80 is transitioned from the flexible, flaccid condition of FIG. 5 to a rigid, erectile condition of FIG. 8, which corresponds to the substantial elimination of fluid 70 from the inner sleeve chamber 92.

The volumetric relationships of the aggregate of filler 108, and fluid 70 relative to the volumetric capacity of the inner sleeve chamber 92 is predetermined to establish rigidification of the chamber 92 when substantially all of the fluid 70, which permits relative movement of the aggregate of filler material 108 in the inner sleeve chamber 92, has been pumped from the inner sleeve chamber 92.

The rigidification of the inner chamber 92 is analogous to the rigidification of a conventional bean bag by eliminating any slack volume from the bean bag, whereby the bean bag takes on the characteristics of a one-piece, rigid structure.

It will also be noted that the amount of fluid present in the inner sleeve chamber 92 to provide the prosthesis with the characteristics of a flaccid penile condition can be used to fill the outer sleeve chamber 94, although this is not necessary to obtain the rigidification of the prosthesis 80.

Thus an erectile condition of the prosthesis 80 can be obtained at a relatively low fluid pressure since rigidification is based upon the withdrawal of fluid from the inner sleeve chamber 92.

The aggregate of filler material 108 in the inner sleeve chamber 92 also operates to limit change in the radial dimension of the inner chamber beyond a predetermined minimum radial magnitude. The minimum radial magnitude of the inner sleeve chamber 92 is predetermined by the amount of the aggregate of filler material 108 in the chamber 92, and the minimum radial magnitude is established when substantially all of the fluid 70 has been eliminated from the inner chamber 92.

To transition the prosthesis 80 from the erectile condition of FIG. 7 to the flaccid condition of FIG. 5, a compressive force is applied to the prosthesis at the valve 106 to distort the valve 106 and the annular closure flap 46 which covers the openings 100, 102 and 104. Fluid can thus flow from the outer sleeve chamber 94, through the pump chamber 96 and into the inner sleeve chamber 92 in a manner similar to that previously described for the prosthesis 10. A gentle manual compression of the main body portion 86 while the valve 106 is being distorted helps facilitate transition of the prosthesis 80 from the erectile condition to the flaccid condition.

Upon movement of the fluid 70 into the inner sleeve chamber 92, the unified rigidity of the aggregate of filler material 108 is altered. Movement of the fluid 70 into the inner chamber 92 and dispersal thereof among the components of the aggregate 108 enable such components to move freely with respect to each other and thereby restore the flexibility of the inner sleeve chamber 92 to a level of flexibility that is analogous to the flaccid condition of the penis.

When the compressive force is removed from the area of the valve 106, the inner sleeve chamber 92 is again sealed by the valve 106 to retain the fluid 70. The presence of the fluid 70 in the inner sleeve chamber 92 ensures such that the flaccid condition of the prosthesis 80 is maintained until the pump chamber 96 is sequentially compressed and decompressed in the manner previously described for transitioning the prosthesis 80 from a flaccid condition to an erectile condition.

Another embodiment of the penile prosthesis is generally indicated by the reference number 120 in FIGS. 9-12. The prosthesis 120 is structurally similar to the prosthesis 80 as indicated by the corresponding reference numbers. However, the prosthesis 120 also includes the corrugated webbing 122 in the outer sleeve chamber 94, arranged in a manner similar to that previously described for the corrugated webbing 64 in the outer sleeve chamber 62 of the prosthesis 10.

The prosthesis 120 thus includes filler material in both the inner sleeve chamber 92 and the outer sleeve chamber 94. The inner and outer sleeve chambers 92 and 94 are both capable of becoming rigidified simultaneously to enable the prosthesis 122 to transition from the flaccid condition of FIG. 9 to the erectile condition of FIG. 11.

For example, in using the prosthesis 120, a predetermined amount of the fluid 70 is disposed in the inner sleeve chamber 92 with the aggregate of filler material 108 to enable the inner sleeve chamber 92 to have the flexibility of a flaccid penile condition.

With a predetermined amount of fluid 70 disposed in the inner sleeve chamber 92, the outer sleeve chamber 94 is substantially devoid of the fluid 70 to enable the outer sleeve chamber to also have the flexibility of a flaccid penile condition. Thus the flaccid condition of the prosthesis 120 corresponds to the presence of fluid 70 in the inner sleeve chamber 92 and the absence of the fluid 70 from the outer sleeve chamber 94.

In using the prosthesis 120 to transition the penis from a flaccid condition to an erectile condition, the distal end 84 is compressed as shown in FIG. 9 to cause any of the fluid 70 in the pump chamber 96 to pass through the openings 100, 102 and 104 into the outer sleeve chamber 94.

A sequential decompression of the pump chamber 96, as shown in FIG. 10, permits the fluid 70 from the inner sleeve chamber 92 to be drawn into the pump chamber 96 in a manner previously described for the prosthesis 80. The fluid 70 drawn into the pump chamber 96 is then sequentially pumped through the openings 100, 102 and 104 into the outer sleeve chamber 94.

As the fluid 70 is withdrawn from the inner sleeve chamber 92, the inner sleeve 88 constricts or collapses around the aggregate of filler material 108 to cause a rigidification of the inner sleeve chamber 92. As the fluid 70 is removed from the inner sleeve chamber 92, it is simultaneously pumped into the outer sleeve chamber 94 to cause a buildup of pressure in the outer sleeve chamber 94 in a manner similar to that previously described for the buildup of pressure and rigidity in the outer sleeve chamber 62 of the prosthesis 10. Thus the rigidification of the inner sleeve chamber and the outer sleeve chamber occur substantially simultaneously and effect a transition of the prosthesis 120 from the flaccid condition of FIG. 9 to the erectile condition of FIG. 10, as shown in dotted outline in FIG. 9.

Restoration of the prosthesis 120 to a flaccid condition from the erectile condition is accomplished by compressing the valve 106 in the manner shown in FIG. 11 to permit fluid to flow from the outer sleeve chamber 94 through the pump chamber 96 and into the inner sleeve chamber 92.

It should be noted that any pressure buildup in the outer sleeve chamber 94 is substantially taken up by the webbing 122 which limits the radial expansion of the chamber 94. Buildup of fluid pressure within the chamber 94 does not result in distension of the outer sleeve 90. Thus the chamber 94 does not undergo a proportional radial volume expansion based on internal pressure buildup and therefore has a predetermined volume. Thus volume expansion beyond a predetermined limit is not transmitted to the penile tissue that surrounds the prosthesis. Therefore, when an erectile condition is developed using any one of the prostheses 10, 80 or 120, discomfort associated with radial volume expansion in penile prostheses of known construction is obviated herein.

Another embodiment of the penile prosthesis is generally indicated by the reference number 130 in FIGS. 13-20.

Referring particularly to FIG. 14, the prosthesis 120 includes a proximal end portion 132, a distal end portion 134 and a main body portion 136.

The proximal end portion 132 includes a stepped end 138 which joins with a proximal end 140 of an outer sleeve 142 of the main body portion 136.

The distal end portion 134 includes a conically tapered section 143 having a gently curved free end portion 144 formed from a soft, medical grade material such as silicone, and a generally cylindrical posterior section 146. The conical section 143 defines a minor hollow space 148 and the cylindrical posterior section 146 defines a pump chamber 150 which communicates with the minor space 148. A Dacron mesh disk 152 can be provided within the minor space 148 to limit radial expansion of the conical end portion 144.

The cylindrical section 146 includes a stepped portion 154 that joins with a distal end 156 of the sleeve 142. The main body portion 136 also includes an inner sleeve 158 coaxial with the outer sleeve 142. A proximal end 160 of the inner sleeve 158 joins a relatively high pressure valve 162 that extends from the proximal end portion 132. A distal end 164 of the sleeve 158 joins to a relatively low pressure valve 166 that extends from the distal end portion 134.

The high pressure valve 162 includes a valve housing 168 with a poppet member 170 having a seal portion 172. The seal portion 172 is normally engaged against a valve seat 174 under the influence of a biasing spring 176. The valve seat 174 includes a valve opening 178. The valve housing 168 also includes a distribution opening 180 that communicates with a passageway 182 formed in the valve housing 168. The passageway 182 communicates with an outer sleeve chamber 184 defined between the inner sleeve 158 and the outer sleeve 142.

The low pressure valve 166, which is a dual valve, includes spaced check valves 186 and 188. The check valve 186 permits outlet flow and the check valve 188 permitting inlet flow. The outlet check valve 186 includes a hollow valve stem 190 received in a central passage 192 of a valve body 194. The valve body 194 is joined to or formed as an extension of the distal end portion 134.

The valve stem 190 is generally cylindrical in shape with an inlet port 196 and an outlet passage 198. A conical, deflectable valve closure flap 200 is joined to the valve stem 190 for circumferential sealing engagement with the valve body 194 along a circular path that is concentric with the valve stem 190.

The inlet check valve 188 includes an annular deflectable shell 202 with a base portion 204 formed with an outlet opening 206. The base portion 204 is joined to the valve body 194 such that the outlet opening 206 communicates with the central passageway 192.

The valve body 194 is formed with at least one passageway 208 that leads to the annular shell 202. An open end portion 210 of the annular shell 202 is disposed in a stepped passageway 212 of the distal end portion 134. The annular shell 202 is freely deflectable from the confines of the stepped passageway 212. A bushing 214 is also provided in the stepped passageway 212 spaced from the open end 210 of the annular shell 202. The stepped passageway 212 and the bushing 214 disposed therein are communicable with the pump chamber 150 in the distal end portion 134.

The main body portion 136 which includes the outer sleeve 142 and the inner sleeve 158, also includes filler means 216 for limiting change in the radial dimension of the inner sleeve 158. Referring particularly to FIGS. 14 and 21-26, the filler means 216 include a plurality of disk members 218 which can be formed of Dacron mesh with a disk thickness of .005 to .010 inch. The disks 218 are spaced a predetermined distance from each other in an inner chamber 220 of the inner sleeve member 158. The periphery of the disks 218 are bonded or otherwise joined to the sleeve 158.

FIGS. 21-26 show in simplified schematic fashion the manner in which the disks 218 can be joined to the sleeve 158. For example, each disk 218 is provided with four peripheral notches 221, 222, 224 and 226. The notches 221-226 are sized to accommodate support rods such as 228, 230, 232 and 234 in a tight-fitting relationship. The support rods 228-234 are fixed at one end into a base plate 236, the opposite ends of the rods 228-234 being free ends. The disks 218 can thus be positioned on the support rods for temporary retention in a predetermined spaced relationship as shown in FIG. 23. The support rods may also be of small enough diameter to pass through the mesh without the addition of notches.

The inner sleeve 158 is then disposed around the outside of the support rods so as to envelop the disks 218. Such envelopment can be accomplished by uncurling a rolled sleeve 158 in the manner shown in FIG. 23. When the sleeve 158 is fully uncurled to straddle the entire length of the support rods 228-234 and the spaced disks 218, the base plate 236 is placed in an oven to fuse or bond the periphery of the disks 218 to the sleeve 158.

The support rods 228-234 are formed of a material such as stainless steel which does not fuse with the disks 218 or the sleeve 158 when the fusion operation takes place.

After fusion of the disks 218 to the sleeve 158 has been completed, the sleeve 158 with the disks 218 bonded thereto is removed from the support rods 228-234 in the manner shown in FIG. 25, yielding the disk and sleeve structure of FIG. 26. Referring to FIGS. 14, 15, 17 and 20, it should be noted that the first disk 218 at each opposite end of the sleeve 158 is recessed within the sleeve 158. Recess or clearance of the first disks 218 from the open ends of the sleeve 158 permits anchoring of the proximal end 160 of the sleeve 158 to the valve housing 168 and anchoring of the distal end 164 of the sleeve 158 to the valve body 194 without any interference between the respective valves 162 and 166 and the disks 218.

In using the prosthesis 130, a predetermined amount of fluid 240 which is similar to the fluid 70, is disposed in the outer sleeve chamber 184 when the prosthesis is in a flexible or flaccid condition corresponding to a flaccid penile condition as shown in FIG. 13.

When an erectile condition is desired, the penis 242 is gently compressed at the area of the pump chamber 150 to pump the fluid 240 from the outer sleeve chamber 184 into the inner sleeve chamber 220 in the manner shown in FIG. 15. Thus pressure exerted against the distal end portion 134 of the prosthesis 130 causes fluid 240 to pass from the pump chamber 150 through the passageway 212 into the opening 210 of the inlet check valve 188 for flow through the outlet opening 206 into the central passageway 192.

Fluid from the central passageway 192 enters the inlet port 196 of the outlet check valve 186, where it is directed through the outlet passage 198 into an initially sealed space 246 (FIG. 14) between the conical flap 200 and the valve body 194. The pressure of the fluid 240 in the initially sealed space 246 causes the conical flap 200 to deflect in the manner shown in FIG. 15 permitting the fluid 240 to flow past the outlet check valve 186 into the inner chamber 220 of the inner sleeve 158.

A sequential decompression of the pump chamber 150, as illustrated in FIG. 17, causes the outlet check valve 186 to close and the inlet check valve 188 to open. Thus the fluid 240 in the outer sleeve chamber 184 can flow through the passage 208 and past the deflected annular shell 202 into the passageway 212 for entry into the pumping chamber 150.

The pumping cycle can then be sequentially repeated to pressurize the inner sleeve chamber 220 until the disks 218 are placed under predetermined tension due to the buildup of pressure in the inner chamber 220. The disks 218 also limit radial expansion of the inner sleeve 158 beyond a predetermined radial magnitude.

During the pumping of the fluid 240 from the outer sleeve chamber 184 into the inner sleeve chamber 220 and the consequential buildup of pressure in the inner sleeve chamber 220, the prosthesis 130 transitions from the flaccid condition of FIG. 13 to the erectile condition of FIG. 19.

When it is desired to transition the prosthesis 130 from the erectile condition to a flaccid condition, the pendulous portion of the penis is compressed in the manner shown in FIGS. 19 and 20. Such compression increases the pressure of the fluid 240 in the inner chamber 220 to a predetermined level which causes opening of the valve 162. The increased pressure of the fluid 240 resulting from manual force being applied to the main body portion 136 of the prosthesis 130, causes the poppet 170 of the valve 162 to unseat from the valve seat 174.

The fluid 240 is thus allowed to flow through the valve opening 178 past the distribution opening 180, into the passageway 182 for disposition in the outer sleeve chamber 184. Preferably the pressure applied to the main body portion 136 of the prosthesis 130 should be intermittent to permit the fluid 240 flowing from the inner sleeve chamber 220 into the outer sleeve chamber 184 to flow past the point of pressure imposed upon the main body portion 136.

The amount of the fluid 240 contained in the prosthesis 130, and the volumetric capacities of the inner and outer chambers 220 and 240 are predetermined to ensure that as the fluid 240 is removed from the inner chamber 220 for passage to the outer chamber 240 the prosthesis 130 transitions from the erectile condition to the flaccid condition to permit the penis to assume a comfortable, flexible, flaccid condition.

The pressure level at which the valve 162 is actuated to open is predetermined to exceed the normal pressure levels that the penis experiences during intercourse. The opening pressure for the valve 162 also exceeds the pressure levels that are needed in the inner sleeve chamber 220 to obtain rigidification of the chamber 220 to thereby place the prosthesis 130 in an erectile condition.

Another embodiment of the penile prosthesis is generally indicated by the reference number 260 in FIGS. 27-32.

The prosthesis 260 includes a proximal end 262, a distal end 264 and a main body portion 266 joining the proximal and distal end portions.

The proximal end portion 262 includes a mounting section 268, a reservoir section 270 and a valve 272. The reservoir section 270 includes a reservoir sleeve 274 having a proximal end 276 joined to a stepped portion 278 of the mounting section 268. A distal end 280 of the reservoir sleeve 274 is joined to the periphery of the valve 272.

The reservoir sleeve 274 defines a reservoir chamber 282 filled with a predetermined amount of fluid 284 similar to the fluid 70. The reservoir sleeve 274, which is formed of any suitable biocompatible material such as Dacron, is in the shape of a bellows, as most clearly shown in FIG. 28.

The distal end 264 of the prosthesis 260 includes a generally cylindrical section 286, with a tapered conical section 288 having a gently curved free end 290 formed of a relatively firm, medical grade material such as silicone.

The main body portion 266 includes a sleeve 292 having a proximal end 294 joined to the periphery of the valve 272 and a distal end 296 joined to a stepped portion 298 of the distal end portion 264. The sleeve 292 defines a sleeve chamber 300.

A plurality of disks 302 similar to the disks 218 can be provided in the chamber 300 at a predetermined spacing from each other in a manner similar to that previously described for the prosthesis 130.

The valve 272, which is similar to the valve 48 includes a ball 304 which is normally biased against a valve seat 306 by a biasing spring 308. The valve 272 also includes an opening 310 opposite the valve seat 306.

In using the prosthesis 260, a predetermined amount of the fluid 284 is disposed in the reservoir chamber 282. When the prosthesis 260 is in a flaccid condition the sleeve chamber 300 is sufficiently depleted of fluid to afford the sleeve chamber 300 the desirable characteristic flexibility of a flaccid penile condition.

Figure 28:
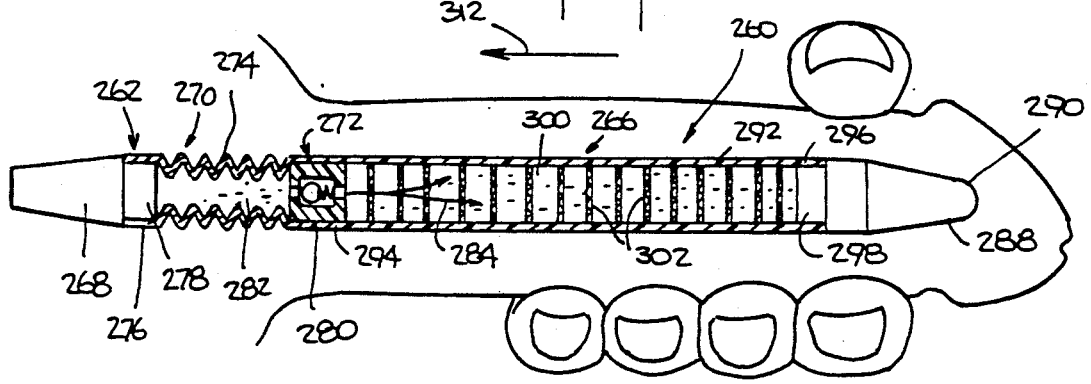
FIG. 28 is a view similar to FIG. 27 during a pumping operation for placing the prosthesis in an erectile condition.
Figure 29:
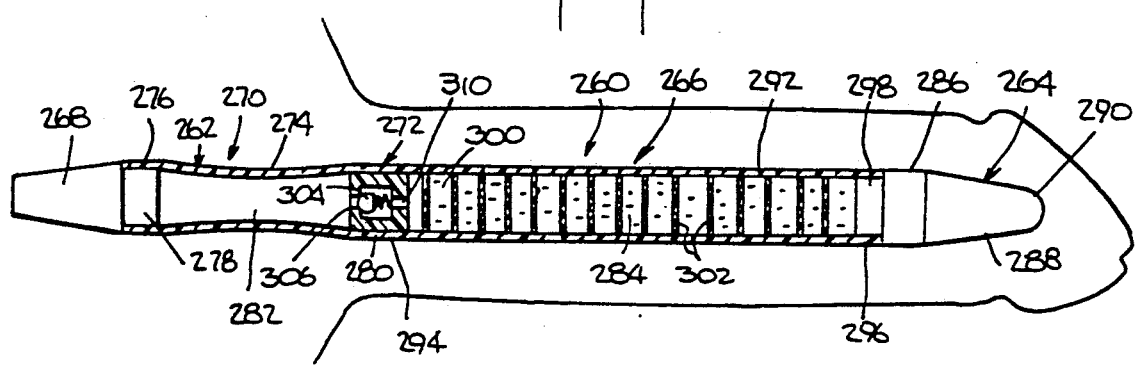
FIG. 29 is a view similar to FIG. 27 showing the prosthesis in an erectile condition.

When it is desired to develop an erectile condition in the penis, the prosthesis 260 is moved in the protractile direction in the manner shown in FIG. 28 by moving the penis in the proximal direction indicated by the arrow 312.

Movement of the prosthesis 260 in the direction indicated by the arrow 312, by corresponding movement of the penis 242, causes the bellows-shaped reservoir sleeve 274 to axially contract. The fluid 284 in the reservoir chamber 282 is thereby placed under sufficient pressure to open the valve 272. The ball 304 thus unseats from the valve seat 306, enabling the fluid 284 to flow past the valve 272 into the sleeve chamber 300. Movement of the prosthesis 260 in the manner previously described operates to pump the fluid 284 from the reservoir chamber 282 into the sleeve chamber 300.

As previously described for the prosthesis 130, the presence of the disks 302 in the sleeve chamber 300 prevent the sleeve chamber from expanding radially beyond a predetermined radial magnitude governed by the diameter of the disks 302. The sleeve 292 thus expands to a condition where the volume of the sleeve 292 becomes fixed such that infusions of fluid into the sleeve 292 as the sleeve reaches full capacity cause rapid buildup of pressure.

The buildup of pressure in the sleeve 292 to a predetermined level effects a rigidification of the chamber 300 enabling the prosthesis 262 to transition from the flaccid condition of FIG. 33 to the erectile condition of FIG. 31.

When it is desired to restore the flaccid condition of the penis 242, pressure is applied through the penis to the prosthesis 260 at the region of the valve 272. Pressure distortion of the valve 272 in the manner shown in FIG. 32 opens the valve and enables the fluid 284 in the chamber 300 to flow back into the reservoir 282. Gentle manual compression of the sleeve 292 helps facilitate flow of the fluid 284 into the reservoir 282.

When a predetermined amount of the fluid 284 has been caused to flow from the chamber 300 back into the reservoir 282, the main body portion 266 is restored to its flexible condition to enable the penis to reassume its flaccid condition. The cycles of flaccidity and rigidity can thus be selected at will.

Another embodiment of the penile prosthesis is generally indicated by the reference number 320 in FIGS. 34-37.

The prosthesis 320 includes a proximal end 322, a distal end 324 and a main body section 326 adjoining the proximal and distal ends 322 and 324.

The proximal end 322 includes a mounting section 328, similar to the mounting section 268 of the prosthesis 260 and a reservoir section 330. A valve 332, similar to the valve 272 of the prosthesis 260 is provided at a distal end of the reservoir section 330. The reservoir section 330 includes a reservoir sleeve 334 that defines a reservoir chamber 336 provided with a predetermined amount of fluid 338, similar to the fluid 70.

The distal end portion 324 of the prosthesis 320 includes a generally hollow conical section 340 which defines a pumping chamber 342. The distal end portion 324 also includes a dual check valve 344 at a proximal end of the pump chamber 342.

The dual check valve 344 includes valve elements 346 and 348 that are identical to the outlet check valve 186 of the prosthesis 130. The valve elements 346 and 348 are disposed in a valve body 350. Thus each of the valve elements 346 and 348 include respective conical flaps 352 and 354. A valve passage 356 formed in the valve body 350 communicates with the valve element 346 and a valve passage 358 in the valve body 350 communicates with the valve element 348.

The main body section 326 includes a sleeve 360 that defines a sleeve chamber 362. The sleeve 360 is joined at a proximal end 364 to the periphery of a valve body 366 of the valve 332. A distal end 368 of the sleeve 360 is joined to the periphery of the valve body 350.

A plurality of flexible disks 370, similar to the disks 218, are provided at a predetermined spacing from each other in the sleeve chamber 362 in a manner similar to that previously described for the prosthesis 130. Each of the disks 370 include an opening sized to accommodate a flexible elongated tube 372 having a proximal end 374 supported in a passageway 376 of the valve body 366. The tube 372 also includes a distal end 378 supported in a passageway 358 of the valve body 350.

The valve 332 includes a spring biased ball 380 normally biased against a valve seat 382. A valve opening 384 is provided opposite the valve seat 382.

In using the prosthesis 320, flaccid or erectile conditions can be developed at will through manual manipulation of the prosthesis.

For example, assuming the prosthesis is in a flaccid condition, substantially the entire supply of fluid 338 is located in the reservoir 336. When an erectile condition is desired, the penis 242 is manipulated in the glans area 244, as shown in FIG. 34, to gently apply a compressive force to the distal end 324. Pressure applied to the distal end 324 causes compression of the pump chamber 342 which forces fluid from the pump chamber 342 into the passageway 356 of the valve body 350 for movement past the valve element 346 into the sleeve chamber 362, as indicated by the arrow 386. Fluid entering the sleeve chamber 362 is normally prevented from exiting the chamber 362 by the valve 332.

A sequential decompression of the pump chamber 342 establishes a suction condition in the pump chamber causing the valve element 348 to open to allow the fluid 338 from the reservoir chamber 336 to pass through the passageway 376 into the tube 372 and into the passageway 358 for movement past the conical flap 352 of the valve element 348 into the pump chamber 342.

The sequential compression and decompression of the pump chamber 342 results in a gradual filling of the sleeve chamber 362 to a radial expansion limit determined by the diameter of the disks 370. The sleeve chamber 362 is thus expanded to a rigidification condition, as described for the prosthesis 130, to transition the prosthesis 320 from the flaccid condition to an erectile condition.

When it is desired to transition the prosthesis 320 from an erectile condition to a flaccid condition, pressure is applied to the root end of the penis as illustrated in FIG. 36 to distort the valve 332. Distortion of the valve 332 enables the fluid 338 in the sleeve chamber 362 to flow past the valve 332 into the reservoir chamber 336.

It should be noted that substantially total removal of fluid from the sleeve chamber 362 can be facilitated by also gently applying manual pressure to the pendulous portion of the penis while the valve 33 is distorted.

Another embodiment of the penile prosthesis is generally indicated by the reference number 390 in FIGS. 38-40. The prosthesis 390 includes a proximal end 392, a distal end 394 and a main body section 396 adjoining the proximal end 392 and the distal end 394. The prosthesis 390 also includes a pump and reservoir section 398 arranged to communicate with the main body section 396 via a flexible conduit 400.

The proximal end 392 is formed with a passageway 402 that communicates with the conduit 400. The proximal end 392 is otherwise formed of a relatively firm, biocompatible, medical grade material such as silicone. The distal end 394, which is also formed of a similar relatively firm, medical grade elastomer, has a generally tapered conical section 404 with a gently curved free end 406.

The main body portion 396 includes a sleeve member 408 having a proximal end 410 joined to a stepped portion 412 of the proximal end portion 392. A distal end 414 of the sleeve member 408 is joined to a stepped portion 416 of the distal end portion 394. The sleeve member 408 defines a sleeve chamber 418 that is communicable with the passageway 402 of the proximal end 392.

A plurality of disks 420, similar to the disks 218 of the prosthesis 130, are disposed in the sleeve chamber 418 at a predetermined spacing from each other.

The reservoir chamber 398 includes a bulb-like shell portion 422 that is flexible and compressible, and is preferably formed of a suitable biocompatible material such as silicone. A valve 424, similar to the valve 272 of the prosthesis 260, is joined to the reservoir shell 422. The valve 424 includes a spring biased ball 426 normally seated against a valve seat 428, and an oppositely disposed valve opening 430 which communicates with the conduit 400.

In using the prosthesis 390, the proximal end 392, the distal end 394 and main body section 396 are implanted in the penis 242 in a manner similar to that previously described for the prosthesis 10. The reservoir section 398 is implanted in the scrotal sac (not shown).

When the prosthesis 390 is in a flaccid condition as shown in FIG. 38, the reservoir shell 422 houses a predetermined supply of fluid 432, similar to the fluid 70, in a chamber 434 of the reservoir, and the sleeve chamber 418 is substantially devoid of fluid. A gentle compression of the reservoir shell 422 in the manner shown in FIG. 39 causes the fluid 432 to unseat the valve ball 426 from the valve seat 428 thereby enabling the fluid 432 to flow through the conduit 400 into the passageway 402 and into the sleeve chamber 418.

The reservoir shell 422 can be compressed once or, if desired, pumped intermittently to transfer a predetermined amount of the fluid 432 into the sleeve chamber 418. Incoming fluid enables the sleeve member 408 to transition to an erectile condition in a manner similar to that previously described for the prosthesis 10. Fluid in the sleeve chamber 418 is normally unable to flow back into the reservoir chamber 432 because the valve 424 is a one-way check valve.

When it is desired to transition the prosthesis 390 from the erectile condition of FIG. 39 to the flaccid condition of FIG. 38, the valve 422 is gently distorted in the manner shown in FIG. 40 by applying pressure through the scrotal sac to the periphery of the valve 424. Distortion of the valve 424 unseats the ball 426 from the valve seat 428. Fluid from the sleeve chamber 418 can thus flow in a reverse direction through the conduit passageway 402, into the tube 400, past the valve 424, and into the reservoir chamber 434. The prosthesis 390 can thus be placed in an erectile condition or flaccid condition at the selection of the user.

Another embodiment of the penile prosthesis is generally indicated by the reference number 480 in FIGS. 41–44. The prosthesis 480 includes a proximal end 482, a distal end 484 and a main body section 486. The prosthesis 480 also includes a reservoir section 488 similar to the reservoir and pump section 398 of the prosthesis 390. The proximal end 482 and the distal end 484 of the prosthesis 480 are similar to the proximal and distal ends 392 and 394 of the prosthesis 390.

The main body section 486 includes a sleeve member 490 joined to the proximal end 482 and the distal end 484 in a manner similar to that previously described for the prosthesis 390. The sleeve member 490 includes a sleeve chamber 492 that is provided with nonsoluble filler members 494 which are substantially spherical in shape. The filler members 494 can be formed of any suitable biocompatible plastic or metal material. In addition, the filler members 494 can be liquid filled hollow spheres.

The spherical filler members 494 need not be of uniform size but can be within a diametrical range of approximately 0.3 cm. Preferably for a sleeve chamber of approximately 1.0 cm in diameter and 12 cm in length, and having a volume of 10 to 12 cc, the approximate volume of the filler members provided in the chamber is approximately 8 to 11 cc.

In using the prosthesis 480, the sleeve chamber 492 is normally filled with a fluid 496, similar to the fluid 70, when the prosthesis is in the flaccid condition. Thus the filler members 494, in the presence of the fluid 496, can shift relative to one another such that the main body section 486 is flexible in a manner that is analogous to the flaccid condition of a penis. The reservoir shell 498 of the pump chamber 488 is in a generally collapsed condition when the sleeve 490 is in the flaccid condition.

The chamber 500 of the reservoir shell 498 is at a relatively low pressure level close to vacuum conditions and is maintained at such relatively low pressure level by the normally closed valve 424.

To transition the prosthesis 480 from the flaccid condition of FIG. 41 to the erectile condition of FIG. 43, the valve 424 is gently distorted in the manner shown in FIG. 43. Distortion of the valve 424 causes the valve to open and thereby permit the fluid 496 in the shell chamber 492, which is at a relatively high pressure, to flow into the reservoir and pump chamber 500 which is at a relatively low pressure. The fluid 496 thus flows continuously out of the sleeve chamber 492 as long as the valve 424 is maintained in an open condition.

The flow of the fluid 496 from the sleeve chamber 492 into the reservoir 500 results in a lowering of fluid pressure in the sleeve chamber 496. The sleeve 490 thus constricts or collapses around filler members 494 thereby binding such filler members together to substantially prevent relative movement between the filler members. As a result, the sleeve chamber 492 rigidifies and causes the main body section 486 to assume an erectile posture as shown in FIG. 43.

When it is desired to restore the flaccid condition of the prosthesis 480, the reservoir shell 498 is gently compressed, preferably in a gentle continuous squeezing action, to unseat the ball of the valve 424 and cause the fluid 496 to flow past the valve 424 through the conduit 400 and passageway 402 into the sleeve chamber 492. The accumulation of fluid 496 in the sleeve chamber 492 expands the sleeve 490 giving the filler members room to move relative to each other thereby restoring the flexible condition of the sleeve member 490 and enabling the penis 242 to assume the flaccid condition shown in FIG. 41.

Some advantages of the present invention evident from the foregoing description include a penile prosthesis that can assume an erectile posture at substantially little or no pressure within the prosthesis. The prosthesis includes filler members for limiting change in the radial dimension of the penile prosthesis chamber as by limiting radial expansion in some embodiments and radial contraction in other embodiments.

The embodiments which have an expandable limit can achieve an erectile condition by pumping fluid into a chamber until the filler members therein are placed under tension to maintain the chamber at a substantially fixed volume. When the chamber is substantially full, small additions of fluid can cause a rapid pressure rise due to the nondistensible characteristics of the chamber walls.

The prosthesis includes provision for pumping at a proximal end portion using axially reciprocative movement. In other embodiments the prosthesis can be pumped at a distal end portion using sequential compression and decompression of a pump chamber, and in other embodiments a pumping chamber is located in a scrotal sac.

Since the pressure within the prosthesis in some embodiments is taken up by filler members that restrict radial expansion of the prosthesis, pressures imposed within the prosthesis are not entirely transferred to the surrounding penile tissue. Thus the comfort of such prostheses is enhanced. In other embodiments where the absence of fluid pressure and expulsion of fluid is a factor in achieving an erectile condition, little if any fluid pressure is imposed on the penile tissue surrounding the prosthesis. Thus greater comfort levels are achieved using the disclosed prostheses than in prostheses that derive rigidity based on a high pressure expansion of an inner chamber.

A further advantage is that the user can select at will a flaccid or erectile condition of the penis.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A penile prosthesis comprising a normally flaccid but selectively rigidifiable axially elongate main body portion, a proximal end portion extending from a corresponding proximal end of the main body portion, and a distal end portion extending from a corresponding distal end of said main body portion, said main body portion including at least one chamber having a fluid fillable space, filler means in said fluid fillable space, pumping means communicable with said one chamber and actuatable for pumping fluid in a predetermined direction between said fluid fillable space and said pumping means, and valve means disposed between said pumping means and said one chamber and cooperable with said pumping means for controlling the predetermined direction of flow of fluid between said one chamber and said pumping means during actuation of said pumping means such that movement of said fluid in said predetermined direction in response to activation of said pumping means cause rigidification of said one chamber, and wherein said filler means includes means for limiting change in the radial magnitude of said one chamber beyond a predetermined amount when said chamber is rigidified.

2. The penile prosthesis as claimed in claim 1 wherein said one chamber is defined by a flexible, collapsible, nondistensible sleeve member and said means for limiting change in the radial magnitude of said one chamber include means for limiting the radial expansion of said sleeve member beyond a predetermined limit.

3. The penile prosthesis as claimed in claim 2 wherein said pumping means is adapted to pump fluid in said predetermined direction into said one chamber to cause rigidification of said one chamber.

4. The penile prosthesis as claimed in claim 2 wherein said means for limiting radial expansion of said sleeve member include at least one filler member having an outer periphery substantially radially coextensive with and joined to said sleeve member.

5. The penile prosthesis as claimed in claim 2 wherein the pumping means are provided in said distal end portion.

6. The penile prosthesis as claimed in claim 2 wherein a conduit joins said pumping means and said distal end portion such that said pumping means is communicable with said one chamber through said conduit.

7. The penile prosthesis as claimed in claim 2 wherein said pumping means are provided in said proximal end portion.

8. The penile prosthesis as claimed in claim 7 wherein said pumping means is in the form of a bellows that is axially contractible along the axis of said elongated main body portion during actuation of said pumping means.

9. A method of selectively establishing a rigid condition in a penile prosthesis having an axially elongated chamber with a flexible wall comprising,
   a. incorporating filler material in a fluid fillable space of said chamber to limit change in radial magnitude of said chamber beyond a predetermined amount, and
   b. causing fluid to move in a predetermined direction between the fluid fillable space of the chamber and a pump in response to actuation of the pump such that said chamber is at said predetermined radial magnitude to enable the filler material, in cooperation with the movement of fluid, to establish a rigid condition in said chamber.

10. The method according to claim 9 including attaching the filler material to the wall of the chamber to restrict radial expansion of the chamber beyond a predetermined magnitude and pumping fluid into the chamber to effect a radially expanded limit condition of the chamber determined by the radial extent of the filler material to cause rigidification of the chamber and the prosthesis.

* * * * *